(12) United States Patent
Penner et al.

(10) Patent No.: US 7,723,075 B2
(45) Date of Patent: May 25, 2010

(54) METHODS OF SCREENING FOR TRPM5 MODULATORS

(75) Inventors: Reinhold Penner, Honolulu, HI (US); Andrea Flieg, Honolulu, HI (US)

(73) Assignee: The Queens's Medical Center, Honolulu, HI (US)

( * ) Notice: Subject to any disclaimer, the term of this patent is extended or adjusted under 35 U.S.C. 154(b) by 422 days.

(21) Appl. No.: 10/785,758

(22) Filed: Feb. 23, 2004

(65) Prior Publication Data

US 2005/0019830 A1 Jan. 27, 2005

Related U.S. Application Data

(60) Provisional application No. 60/448,955, filed on Feb. 21, 2003.

(51) Int. Cl.
C12P 21/04 (2006.01)
(52) U.S. Cl. ........................... 435/70.1; 435/41
(58) Field of Classification Search .................. 435/9.1, 435/6, 7.1, 7.2; 436/501
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,117,417 A | 9/2000 | Wicks et al. | |
| 6,641,997 B1 * | 11/2003 | MacKinnon | 435/6 |
| 7,341,842 B2 * | 3/2008 | Margolskee et al. | 435/7.2 |
| 2002/0164645 A1 | 11/2002 | Zuker et al. | |
| 2003/0114510 A1 * | 6/2003 | Ingram et al. | 514/417 |
| 2007/0111264 A1 | 5/2007 | Bryant et al. | |

FOREIGN PATENT DOCUMENTS

| | | |
|---|---|---|
| WO | WO 91/00360 A1 | 1/1991 |
| WO | WO 92/00373 A1 | 9/1992 |
| WO | WO 01/32693 A2 | 5/2001 |
| WO | WO 01/32693 A3 | 5/2001 |
| WO | WO 01/79448 A2 | 10/2001 |
| WO | WO 02/054069 A1 | 7/2002 |

OTHER PUBLICATIONS

Prawitt et al. PNAS 2003 vol. 100 p. 15166-15171.*
Hofmann et al. Current Biology 2003 vol. 13, p. 1153-1158.*
Alvarez-Barrientos, A., et al., "Applications of flow cytometry to clinical microbiology," *Clin. Microbiol. Rev.* 13(2):167-195 (Apr. 2000).
Boerner, P., et al., "Production of antigen-specific human monoclonal antibodies from in vitro-primed human splenocytes," *J. Immunol.* 147(1):86-95 (Jul. 1991).
Clapham, D., et al., "The TRP ion channel family," *Nat. Rev. Neurosci.* 2(6):387-396 (Jun. 2001).
David, G., et al., "Protein iodination-with solid state lactoperoxidase," *Biochemistry* 13(5):1014 (Feb. 1974).
Devereux, J., et al., "A comprehensive set of sequence analysis programs for the VAX," *Nucleic Acids Res.* 12(1 Pt 1):387-395 (Jan. 1984).
Enklaar, T., et al., "MTR1, a novel biallelically expressed gene in the center of the mouse distal chromosome 7 imprinting cluster, is a member of the TRP gene family," *Genomics* 67(2):179-187 (Jul. 2000).
Feng, D., et al., "Progressive sequence alignment as a prerequisite to correct phylogenetic trees," *J. Mol. Evol.* 25(4):351-360 (1987).
Fishwild, D., et al., "High-avidity human IgG kappa monoclonal antibodies from a novel strain of minilocus transgenic mice," *Nat. Biotechnol.* 14(7):846-861 (Jul. 1996).
Gilbertson, T., et al., "The molecular physiology of taste transduction," *Curr. Opin. Neurobiol.* 10:519-527 (Aug. 2000).
Gilon, P., et al., "Control mechanisms of the oscillations of insulin secretion in vitro and in vivo," *Diabetes* 51(Supp 1):S144-S151 (2002).
Goeger, D., et al., "Cyclopiazonic acid inhibition of the Ca2+-transport ATPase in rat skeletal muscle sarcoplasmic reticulum vesicles," *Biochem. Pharmacol.* 37(5):978-981 (Mar. 1988).
Graham, F., et al., "Characteristics of a human cell line transformed by DNA from human adenovirus type 5." *J. Gen. Virol.* 36(1):59-74 (Jul. 1977).
Harteneck, C., et al., "From worm to main: three subfamilies of TRP channels," *Trends Neurosci.* 23:159-166 (2000).
Hoogenboom; H., et al., "By-passing immunisation: Human antibodies from synthetic repertoires of germline VH gene segments rearranged in vitro." *J. Mol. Biol.* 227(2):381-388 (Sep. 1992).
Hoth, M., et al., "Calcium release-activated calcium current in rat mast cells," *J. Physiol.* 465:359-386 (Jun. 1993).
Hoth, M., et al., "Depletion of intracellular calcium stores activates a calcium current in mast cells," *Nature* 355(6358):353-356 (Jan. 1992).
Hunter, W., et al., "Preparation of iodine-131 labelled human growth hormone of high specific activity," *Nature* 144:495-496 (May 1962).
Irminger, J., et al., "Identification of differentially expressed genes in islets of diabetic GK rats, using subtractive hybridization," *38th EASD Annu. Mtg.*, Abstract #444, 2002.

(Continued)

*Primary Examiner*—Jacob Cheu
(74) *Attorney, Agent, or Firm*—Morgan Lewis & Bockius LLP

(57) ABSTRACT

The invention relates to methods useful in identifying molecules that bind TRPM5, which modulate TRPM5 ion channel activity, and/or which alter expression of TRPM5 within cells. The TRPM5 channels as described herein contain TRPM5 polypeptides, which are in turn encoded by TRPM5 nucleic acids. The ion channels described herein are preferably formed in HEK-293 cells from one or more novel TRPM5 polypeptides, which exhibit one or more of the unique TRPM5 properties described herein.

26 Claims, 7 Drawing Sheets

OTHER PUBLICATIONS

Jones, P., et al., "Replacing the complementarity-determining regions in a human antibody with those from a mouse," *Nature* 321(6069):522-525 (May 1986).

Karlin, S., et al., "Applications and statistics for multiple high-scoring segments in molecular sequences," *Proc. Natl. Acad. Sci. USA* 90(12):5873-5877 (Jun. 1993).

Köhler, G., et al. "Continuous cultures of fused cells secreting antibody of predefined specificity," *Nature* 256(5577):495-497 (Aug. 19750.

Kozbor, D., "A human hybrid myeloma for production of human monoclonal antibodies." *J. Immunol.* 133(60:3001-3005 (Dec. 1984).

Launay, P., et al., "TRPM4 is a Ca2+-activated nonselective cation channel mediating cell membrane depolarization," *Cell* 109(3):397-407 (May 2002).

Lonberg, N., et al., "Antigen-specific human antibodies from mice comprising four distinct genetic modifications," *Nature* 368(6474):856-859 (Apr. 19940.

Lonberg, N., et al., "Human antibodies from transgenic mice," *Int. Rev. Immunol.* 13(1):65-93 (1995).

Margolskee, R., "Molecular mechanisms of bitter and sweet taste transduction," *J. Biol. Chem.* 277(10:1-4 (Jan. 2002) (first e-pub'd Nov. 5, 2001).

Marks, J., et al., "Bypassing immunization: Building high affinity human antibodies by chain shuffling," *Biotechnology* 10(&):779-783 (Jul. 1992).

Marks, J., et al., "By-passing immunization: Human antibodies from V-gene libraries displayed on phage," *J. Mol. Biol.* 222(3):581-597 (Dec. 1991).

Mather, J., et al., "Establishment and characterization of two distinct mouse testicular epithelial cell lines," *Biol. Reprod.* 23(1):243-252 (Aug. 1980).

Minke, B., et al., "TRP channel proteins and signal transduction," *Physiol. Rev.* 82:429-472 (2002).

Montell, C., et al., "A unified nomenclature for the superfamily of TRP cation channels," *Mol. Cell* 9:229-231 (2002).

Montell, C., et al., "The TRP channels, a remarkably functional family," *Cell* 108(5):595-598 (Mar. 2002).

Morrison, S., et al., "Immunology. Success in specification," *Nature* 368(6414):812-813 (Apr. 1994).

Munson, P.. et al., "Ligand: a versatile computerized approach for characterization of ligand-binding systems," *Anal. Biochem.* 107(1):220-239 (Sep. 1990).

Nadler; M., et al., "LTRPC7 is a Mg.ATP-regulated divalent cation channel required for cell viability," *Nature* 411(6837):590-5895 (May 2001).

Neuberger, M., "Generating high-avidity human Mabs in mice," *Nat. Biotechnol.* 14(&):826 (Jul. 1996).

Nygren, H., "Conjugation of horseradish peroxidase to Fab fragments with different homobifunctional and hterobifunctional cross-linking reagents. A comparative study." *J. Histochem. Cytochem.* 30(5):407-412 (May 1982).

Pain, D., et al., "Preparation of protein A-peroxidase monoconjugate using a heterobifunctional reagent, and its use in enzyme immunoassays," *J. Immunol. Meth.* 40(2):219-230 (Jan. 1981).

Parekh, A., et al., "Store depletion and calcium influx," *Physiol. Rev.* 77:901-930 (1997).

Parekh, A., et al., "The store-operated calcium current IcRAc: non-linear activation by InsP3 and dissociation from calcium release," *Cell* 89:973-980 (1997).

Pearson, W., et al., "Improved tools for biological sequence comparison," *Proc. Natl. Acad. Sci. USA*. 85(8):2444-2448 (Apr. 1988).

Pérez, C., et al., "A transient receptor potential channel expressed in taste receptor cells," *Nat. Neurosci.* 5(11):1169-1176 (Nov. 2002) (first e-pub'd Oct. 7, 2002).

Picking, W., et al., "Control of *Drosphila opsin* gene expression by carotenoids and retinoic acid: northern and western analyses," *Exp. Eye Res.* 65(5):717-727 (Nov. 1997).

Prawitt, D., et al., "Identification and characterization of MTR1, a novel gene with homology to melastatin (MLSN1) and the TRP gene family located in the MWS-WT2 critical region on chromosome 1 1p15.5 and showing allele-specific expression," *Hum. Mol. Genet.* 9:203-216 (2000).

Urlaub, G., et al., "Isolation of Chinese hamster cell mutants deficient in dihydrofolate reductase activity," *Proc. Natl. Acad. Sci. USA* 77(7):4216-4220 (Jul. 1980).

Verhoeyen, M., et al., "Reshaping human antibodies: grafting an antilysozyme acitivty," *Science* 239(4847):1534-1536 (Mar. 1986).

Zamecnik, P., et al., "Inhibition of replication and expression of human T-cell lymphotropic virus type III in cultured cells by exogenous synthetic oligonucleotides complementary to viral RNA," *Proc. Natl. Acad. Sci. USA* 83(12):4143-4146 (Jun. 1986).

Zhang, Y., et al., "Coding a sweet, bitter, and umami tastes: different receptor cells sharing similar signaling pathways," *Cell* 112(3):293-301 (Feb. 2003).

* cited by examiner

```
   1 gaggccacca tgcaggatgt ccaaggcccc cgtcccggaa gccccgggga tgctgaagac
  61 cggcgggagc tgggcttgca caggggcgag gtcaactttg gagggtctgg gaagaagcga
 121 ggcaagtttg tacgggtgcc gagcggagtg gccccgtctg tgctctttga cctgctgctt
 181 gctgagtggc acctgccggc ccccaacctg tggtgtccc tggtgggtga ggagcagcct
 241 ttcgccatga agtcctggct gcgggatgtg ctgcgcaagg ggctggtgaa ggcggctcag
 301 agcacaggag cctggatcct gaccagtgcc ctccgcgtgg gcctggccag gcatgtcggg
 361 caggccgtgc gcgaccactc gctggccagc acgtccacca aggtccgtgt ggttgctgtc
 421 ggcatggcct cgctgggccg cgtcctgcac cgccgcattc tggaggaggc ccaggaggat
 481 tttcctgtcc actaccctga ggatgacggc ggcagccagg gccccctctg ttcactggac
 541 agcaacctct cccacttcat cctggtggag ccaggccccc cggggaaggg cgatgggctg
 601 acggagctgc ggctgaggct ggagaagcac atctcggagc agagggcggg ctacggggc
 661 actggcagca tcgagatccc tgtcctctgc ttgctggtca atggtgatcc caacaccttg
 721 gagaggatct ccagggccgt ggagcaggct gccccgtggc tgatcctggt aggctcgggg
 781 ggcatcgccg atgtgcttgc tgccctagtg aaccagcccc acctcctggt gcccaaggtg
 841 gccgagaagc agtttaagga gaagttcccc agcaagcatt tctcttggga ggacatcgtg
 901 cgctggacca agctgctgca gaacatcacc tcacaccagc acctgctcac cgtgtatgac
 961 ttcgagcagg agggctccga ggagctggac acggtcatcc tgaaggcgct ggtgaaagcc
1021 tgcaagagcc acagccagga gcctcaggac tatctggatg agctcaagct ggccgtggcc
1081 tgggaccgcg tggacatcgc caagagtgag atcttcaatg ggacgtgga gtggaagtcc
1141 tgtgacctgg aggaggtgat ggtggacgcc ctggtcagca acaagcccga gtttgtgcgc
1201 ctctttgtgg acaacggcgc agacgtggcc gacttcctga cgtatgggcg gctgcaggag
1261 ctctaccgct ccgtgtcacg caagagcctg ctcttcgacc tgctgcagcg aagcaggag
1321 gaggccggc tgacgctggc cggcctgggc acccagcagg cccgggagc acccgcgggg
1381 ccaccggcct tctccctgca cgaggtctcc cgcgtactca aggactcct gcaggacgcc
1441 tgccgaggct ctaccaggac cggccggcca ggggaccgca ggagggcgga gaagggcccg
1501 gccaagcggc ccacgggcca gaagtggctg ctggacctga accagaagag cgagaacccc
1561 tggcgggacc tgttcctgtg ggccgtgctg cagaaccgcc acgagatggc cacctacttc
1621 tgggccatgg gccaggaagg tgtggcagcc gcactggccg cctgcaaaat cctcaaagag
1681 atgtcgcacc tggagacgga ggccgaggcg gccccgagcca cgcgcgaggc gaaatacgag
1741 cggctggccc ttgacctctt ctccgagtgc tacagcaaca gtgaggcccg cgccttcgcc
1801 ctgctgctgc gccggaaccg ctgctggagc aagaccacct gcctgcacct ggccaccgag
1861 gctgacgcca aggccttctt tgcccacgac ggcgttcagg ccttcctgac caggatctgg
1921 tggggggaca tggccgcagg cacgcccatc ctgcggctgc taggagcctt cctctgcccc
1981 gccctcgtct ataccaacct catcaccttc agtgaggaag ctccccctgag acaggcctg
2041 gaggacctgc aggacctgga cagcctggac acggagaaga gcccgctgta tggccctgcag
2101 agccgggtgg aggagctggt ggaggcgccg agggctcagg gtgaccgagg cccacgtgct
2161 gtcttcctgc tcacacgctg gcggaaattc tggggcgctc ccgtgactgt gttcctgggg
2221 aacgtggtca tgtacttcgc cttcctcttc ctgttcacct acgtcctgct ggtggacttc
2281 aggcgctgcc cccagggccc ctcagggccc tctacttctg ggtctttacg
2341 ctggtgctgg aggaaatccg gcaggcttc ttcacagacg aggacacaca cctggtgaag
2401 aagttcacac tgtatgtggg ggacaactgg aacaagtgtg acatggtggc catcttcctg
2461 ttcatcgtgg gtgtcacctg caggatgctg ccgtcggcgt ttgaggctgg ccgcacggtc
2521 ctcgccatgg acttcatggt gttcacgctg cggctgatcc atatctttgc catacacaag
2581 cagctgggcc ccaagatcat cgtggtagag cgcatgatga aggacgtctt cttcttcctc
2641 ttctttctga gcgtgtggct cgtggcctac ggtgtcacca cccaggcgct gctgcaccc
2701 catgacgccc gcctggagtg gatcttccgc cgggtgctct accggcccta cctgcagatc
2761 ttcggccaga tcccactgga cgagattgat gaagcccgtg tgaacctgtc cacccaccca
2821 ctgctgctga aggactcacc atcctgcccc agcctctatg ccaactggct ggtcatcctc
2881 ctgctggtca ccttcctgtt ggtcaccaat gtgctgctca tgaacctgct catcgccatg
2941 ttcagctaca cgttccaggt ggtgcagggc aacgcagaca tgttctggaa gttccagcgc
3001 tacaacctga ttgtggagta ccacgagcgc cccgccctgg ccccgccctt catcctgctc
3061 agccacctga gcctgacgct ccgccgggtc ttcaagaagg aggctgagca caagcgggag
3121 cacctggaga gagacctgcc agaccccctg gaccagaagg tcgtcacctg ggagacagtc
3181 cagaaggaga acttcctgag caagatggag aagcggagga gggacagcga ggggaggtg
3241 ctgcggaaaa ccgcccacag agtggacttc attgccaagt acctggggg gctgagagag
3301 caagaaaagc gcatcaagtg tctgagtca cagatcaact actgctcggt gctcgtgtcc
3361 tccgtggctg acgtgctggc ccagggtggc ggccccgga gctctcagca ctgtgggag
3421 ggaagccagc tggtggctgc tgaccacaga ggtggtttag atggctggga caacccgggg
3481 gctggccagc ctccctcgga cacatgagct gcttggcctg ccacgtgtgg gccacctct
3541 cttcagttgg ccaccctgca cgttgtgcac tgacctttgc cgacctccag cggaaccccc
3601 caggggcac cagcccccca gcagacaatg ccctcctgg tgcctcacca cagaccctca
3661 cccaaaggaa ccgctccttg tccctcctgg cctcccggga ggcacagcag tgtcatgggg
3721 ctgtctcccc tgacaggcac aactccccgg gcagaaaacg tgccccaccg catccctacc
3781 tggaaactga ccagcctgca ctgtggaaaa gctggccctg tggcgtgacg ggggagcacc
3841 cccatccaga ctgcgaagct gctctgggtc tgcacccacc cctgccctga cttgtgttgc
3901 ctgacaagag act
```

FIGURE 6

```
   1 mqdvqgprpg spgdaedrre lglhrgevnf ggsgkkrgkf vrvpsgvaps vlfdlllaew
  61 hlpapnlvvs lvgeeqpfam kswlrdvlrk glvkaaqstg awiltsalrv glarhvgqav
 121 rdhslastst kvrvvavgma slgrvlhrri leeaqedfpv hypeddggsq gplcsldsnl
 181 shfilvepgp pgkgdgltel rlrlekhise qragyggtgs ieipvlcllv ngdpntleri
 241 sraveqaapw lilvgsggia dvlaalvnqp hllvpkvaek qfkekfpskh fswedivrwt
 301 kllqnitshq hlltvydfeq egseeldtvi lkalvkacks hsqepqdyld elklavawdr
 361 vdiakseifn gdvewkscdl eevmvdalvs nkpefvrlfv dngadvadfl tygrlqelyr
 421 svsrksllfd llqrkqeear ltlaglgtqq areppagppa fslhevsrvl kdflqdacrg
 481 fyqdgrpgdr rraekgpakr ptgqkwlldl nqksenpwrd lflwavlqnr hematyfwam
 541 gqegvaaala ackilkemsh leteaeaara treakyerla ldlfsecysn searafallv
 601 rrnrcwsktt clhlateada kaffahdgvq afltriwwgd maagtpilrl lgaflcpalv
 661 ytnlitfsee aplrtgledl qdldsldtek splyglqsrv eelveapraq gdrgpravfl
 721 ltrwrkfwga pvtvflgnvv myfaflflft yvllvdfrpp pqgpsgpevt lyfwvftlvl
 781 eeirqgfftd edthlvkkft lyvgdnwnkc dmvaiflfiv gvtcrmlpsa feagrtvlam
 841 dfmvftlrli hifaihkqlg pkiivvermm kdvffflffl svwlvaygvt tqallhphdg
 901 rlewifrrvl yrpylqifgq ipldeidear vncsthplll edspscpsly anwlvilllv
 961 tfllvtnvll mnlliamfsy tfqvvqgnad mfwkfqrynl iveyherpal appfillshl
1021 sltlrrvfkk eaehkrehle rdlpdpldqk vvtwetvqke nflskmekrr rdsegevlrk
1081 tahrvdfiak ylgglreqek rikclesqin ycsvlvssva dvlaqgggpr ssqhcgegsq
1141 lvaadhrggl dgweqpgagq ppsdt
```

FIGURE 7

SEQUENCE LISTING

<160> NUMBER OF SEQ ID NOS: 4

<210> SEQ ID NO 1
<211> LENGTH: 3913
<212> TYPE: DNA
<213> ORGANISM: Homo sapiens

<400> SEQUENCE: 1

| | | | | | |
|---|---|---|---|---|---|
| gaggccacca | tgcaggatgt | ccaaggcccc | cgtcccggaa | gccccgggga | tgctgaagac | 60 |
| cggcgggagc | tgggcttgca | caggggcgag | gtcaactttg | gagggtctgg | aagaagcga | 120 |
| ggcaagtttg | tacgggtgcc | gagcggagtg | gccccgtctg | tgctctttga | cctgctgctt | 180 |
| gctgagtgga | acctgccggc | ccccaacctg | gtggtgtccc | tggtgggtga | ggagcagcct | 240 |
| ttcgccatga | agtcctggct | gcgggatgtg | ctgcgcaagg | ggctggtgaa | ggcggctcag | 300 |
| agcacaggag | cctggatcct | gaccagtgcc | ctccgcgtgg | gcctggccag | gcatgtcggg | 360 |
| caggccgtgc | gcgaccactc | gctggccagc | acgtccacca | aggtccgtgt | ggttgctgtc | 420 |
| ggcatggcct | cgctgggccg | cgtcctgcac | cgccgcattc | tggaggaggc | ccaggaggat | 480 |
| tttcctgtcc | actaccctga | ggatgacggc | ggcagccagg | gccccctctg | ttcactggac | 540 |
| agcaacctct | cccacttcat | cctggtggag | ccaggccccc | cggggaaggg | cgatgggctg | 600 |
| acggagctgc | ggctgaggct | ggagaagcac | atctcggagc | agagggcggg | ctacggggc | 660 |
| actggcagca | tcgagatccc | tgtcctctgc | ttgctggtca | atggtgatcc | caacaccttg | 720 |
| gagaggatct | ccagggccgt | ggagcaggct | gccccgtggc | tgatcctggt | aggctcgggg | 780 |
| ggcatcgccg | atgtgcttgc | tgccctagtg | aaccagcccc | acctcctggt | gcccaaggtg | 840 |
| gccgagaagc | agtttaagga | gaagttcccc | agcaagcatt | tctcttggga | ggacatcgtg | 900 |
| cgctggacca | gctgctgca | gaacatcacc | tcacaccagc | acctgctcac | cgtgtatgac | 960 |
| ttcgagcagg | agggctccga | ggagctggac | acggtcatcc | tgaaggcgct | ggtgaaagcc | 1020 |
| tgcaagagcc | acagccagga | gcctcaggac | tatctggatg | agctcaagct | ggccgtggcc | 1080 |
| tgggaccgcg | tggacatcgc | caagagtgag | atcttcaatg | gggacgtgga | gtggaagtcc | 1140 |
| tgtgacctgg | aggaggtgat | ggtggacgcc | ctggtcagca | acaagcccga | gtttgtgcgc | 1200 |
| ctctttgtgg | acaacggcgc | agacgtggcc | gacttcctga | cgtatgggcg | gctgcaggag | 1260 |
| ctctaccgct | ccgtgtcacg | caagagcctg | ctcttcgacc | tgctgcagcg | gaagcaggag | 1320 |
| gaggcccggc | tgacgctggc | cggcctgggc | acccagcagg | cccgggagcc | acccgcgggg | 1380 |
| ccaccggcct | tctccctgca | cgaggtctcc | cgcgtactca | aggacttcct | gcaggacgcc | 1440 |
| tgccgaggct | tctaccagga | cggccggcca | ggggaccgca | ggaggggcgga | aagggcccg | 1500 |
| gccaagcggc | ccacgggcca | gaagtggctg | ctggacctga | accagaagag | cgagaacccc | 1560 |
| tggcgggacc | tgttcctgtg | ggccgtgctg | cagaaccgcc | acgagatggc | cacctacttc | 1620 |
| tgggccatgg | gccaggaagg | tgtggcagcc | gcactggccg | cctgcaaaat | cctcaaagag | 1680 |
| atgtcgcacc | tggagacgga | ggccgaggcg | gcccgagcca | cgcgcgaggc | gaaatacgag | 1740 |
| cggctggccc | ttgacctctt | ctccgagtgc | tacagcaaca | gtgaggcccg | cgccttcgcc | 1800 |
| ctgctggtgc | gccggaaccg | ctgctggagc | aagaccacct | gcctgcacct | ggccaccgag | 1860 |
| gctgacgcca | aggccttctt | tgcccacgac | ggcgttcagg | ccttcctgac | caggatctgg | 1920 |
| tggggggaca | tggccgcagg | cacgccatc | ctgcggctgc | taggagcctt | cctctgcccc | 1980 |
| gccctcgtct | ataccaacct | catcacccttc | agtgaggaag | ctcccctgag | acaggcctg | 2040 |

-continued

```
gaggacctgc aggacctgga cagcctggac acggagaaga gcccgctgta tggcctgcag    2100
agccgggtgg aggagctggt ggaggcgccg agggctcagg gtgaccgagg cccacgtgct    2160
gtcttcctgc tcacacgctg gcggaaattc tggggcgctc ccgtgactgt gttcctgggg    2220
aacgtggtca tgtacttcgc cttcctcttc ctgttcacct acgtcctgct ggtggacttc    2280
aggccgcccc cccagggccc ctcagggccc gaggtcaccc tctacttctg ggtctttacg    2340
ctggtgctgg aggaaatccg gcagggcttc ttcacagacg aggacacaca cctggtgaag    2400
aagttcacac tgtatgtggg ggacaactgg aacaagtgtg acatggtggc catcttcctg    2460
ttcatcgtgg gtgtcacctg caggatgctg ccgtcggcgt ttgaggctgg ccgcacggtc    2520
ctcgccatgg acttcatggt gttcacgctg cggctgatcc atatctttgc catacacaag    2580
cagctgggcc ccaagatcat cgtggtagag cgcatgatga aggacgtctt cttcttcctc    2640
ttctttctga gcgtgtggct cgtggcctac ggtgtcacca cccaggcgct gctgcacccc    2700
catgacggcc gcctggagtg gatcttccgc cgggtgctct accggcccta cctgcagatc    2760
ttcggccaga tcccactgga cgagattgat gaagcccgtg tgaactgctc cacccaccca    2820
ctgctgctgg aggactcacc atcctgcccc agcctctatg ccaactggct ggtcatcctc    2880
ctgctggtca ccttcctgtt ggtcaccaat gtgctgctca tgaacctgct catcgccatg    2940
ttcagctaca cgttccaggt ggtgcagggc aacgcagaca tgttctggaa gttccagcgc    3000
tacaacctga ttgtggagta ccacgagcgc cccgccctgg ccccgccctt catcctgctc    3060
agccacctga gcctgacgct ccgccgggtc ttcaagaagg aggctgagca caagcgggag    3120
cacctggaga gagacctgcc agacccccctg gaccagaagg tcgtcacctg ggagacagtc    3180
cagaaggaga acttcctgag caagatggag aagcggagga gggacagcga gggggaggtg    3240
ctgcggaaaa ccgcccacag agtggacttc attgccaagt acctcggggg gctgagagag    3300
caagaaaagc gcatcaagtg tctggagtca cagatcaact actgctcggt gctcgtgtcc    3360
tccgtggctg acgtgctggc ccagggtggc ggccccggga gctctcagca ctgtggcgag    3420
ggaagccagc tggtggctgc tgaccacaga ggtggtttag atggctggga acaacccggg    3480
gctggccagc ctccctcgga cacatgagct gcttggcctg ccacgtgtgg ggccacctct    3540
cttcagttgg ccaccctgca cgttgtgcac tgaccttttgc cgacctccag cggaaccccc    3600
caggggcac cagccccca gcagacaatg ccctcctgg tgcctcacca cagaccctca    3660
cccaaaggaa ccgctccttg tccctcctgg cctccccgga ggcacagcag tgtcatgggg    3720
ctgtctcccc tgacaggcac aactccccgg gcagaaaacg tgccccaccg catccctacc    3780
tggaaactga ccagcctgca ctgtggaaaa gctggccctg tggcgtgacg ggggagcacc    3840
cccatccaga ctgcgaagct gctctgggtc tgcacccacc cctgccctga cttgtgttgc    3900
ctgacaagag act                                                       3913
```

<210> SEQ ID NO 2
<211> LENGTH: 1165
<212> TYPE: PRT
<213> ORGANISM: Homo sapiens

<400> SEQUENCE: 2

```
Met Gln Asp Val Gln Gly Pro Arg Pro Gly Ser Pro Gly Asp Ala Glu
1               5                   10                  15

Asp Arg Arg Glu Leu Gly Leu His Arg Gly Glu Val Asn Phe Gly Gly
            20                  25                  30
```

-continued

```
Ser Gly Lys Lys Arg Gly Lys Phe Val Arg Val Pro Ser Gly Val Ala
        35                  40                  45

Pro Ser Val Leu Phe Asp Leu Leu Ala Glu Trp His Leu Pro Ala
 50                  55                  60

Pro Asn Leu Val Val Ser Leu Val Gly Glu Glu Gln Pro Phe Ala Met
65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu Arg Val Gly Leu
        100                 105                 110

Ala Arg His Val Gly Gln Ala Val Arg Asp His Ser Leu Ala Ser Thr
        115                 120                 125

Ser Thr Lys Val Arg Val Ala Val Gly Met Ala Ser Leu Gly Arg
        130                 135                 140

Val Leu His Arg Arg Ile Leu Glu Glu Ala Gln Glu Asp Phe Pro Val
145                 150                 155                 160

His Tyr Pro Glu Asp Asp Gly Gly Ser Gln Gly Pro Leu Cys Ser Leu
                165                 170                 175

Asp Ser Asn Leu Ser His Phe Ile Leu Val Glu Pro Gly Pro Pro Gly
        180                 185                 190

Lys Gly Asp Gly Leu Thr Glu Leu Arg Leu Arg Leu Glu Lys His Ile
        195                 200                 205

Ser Glu Gln Arg Ala Gly Tyr Gly Gly Thr Gly Ser Ile Glu Ile Pro
        210                 215                 220

Val Leu Cys Leu Leu Val Asn Gly Asp Pro Asn Thr Leu Glu Arg Ile
225                 230                 235                 240

Ser Arg Ala Val Glu Gln Ala Ala Pro Trp Leu Ile Leu Val Gly Ser
                245                 250                 255

Gly Gly Ile Ala Asp Val Leu Ala Ala Leu Val Asn Gln Pro His Leu
        260                 265                 270

Leu Val Pro Lys Val Ala Glu Lys Gln Phe Lys Glu Lys Phe Pro Ser
        275                 280                 285

Lys His Phe Ser Trp Glu Asp Ile Val Arg Trp Thr Lys Leu Leu Gln
        290                 295                 300

Asn Ile Thr Ser His Gln His Leu Leu Thr Val Tyr Asp Phe Glu Gln
305                 310                 315                 320

Glu Gly Ser Glu Glu Leu Asp Thr Val Ile Leu Lys Ala Leu Val Lys
                325                 330                 335

Ala Cys Lys Ser His Ser Gln Glu Pro Gln Asp Tyr Leu Asp Glu Leu
        340                 345                 350

Lys Leu Ala Val Ala Trp Asp Arg Val Asp Ile Ala Lys Ser Glu Ile
        355                 360                 365

Phe Asn Gly Asp Val Glu Trp Lys Ser Cys Asp Leu Glu Glu Val Met
        370                 375                 380

Val Asp Ala Leu Val Ser Asn Lys Pro Glu Phe Val Arg Leu Phe Val
385                 390                 395                 400

Asp Asn Gly Ala Asp Val Ala Asp Phe Leu Thr Tyr Gly Arg Leu Gln
                405                 410                 415

Glu Leu Tyr Arg Ser Val Ser Arg Lys Ser Leu Leu Phe Asp Leu Leu
        420                 425                 430

Gln Arg Lys Gln Glu Glu Ala Arg Leu Thr Leu Ala Gly Leu Gly Thr
        435                 440                 445

Gln Gln Ala Arg Glu Pro Pro Ala Gly Pro Pro Ala Phe Ser Leu His
```

```
            450                 455                 460
Glu Val Ser Arg Val Leu Lys Asp Phe Leu Gln Asp Ala Cys Arg Gly
465                 470                 475                 480

Phe Tyr Gln Asp Gly Arg Pro Gly Asp Arg Arg Ala Glu Lys Gly
                485                 490                 495

Pro Ala Lys Arg Pro Thr Gly Gln Lys Trp Leu Leu Asp Leu Asn Gln
                500                 505                 510

Lys Ser Glu Asn Pro Trp Arg Asp Leu Phe Leu Trp Ala Val Leu Gln
            515                 520                 525

Asn Arg His Glu Met Ala Thr Tyr Phe Trp Ala Met Gly Gln Glu Gly
            530                 535                 540

Val Ala Ala Ala Leu Ala Ala Cys Lys Ile Leu Lys Glu Met Ser His
545                 550                 555                 560

Leu Glu Thr Glu Ala Glu Ala Arg Ala Thr Arg Glu Ala Lys Tyr
                565                 570                 575

Glu Arg Leu Ala Leu Asp Leu Phe Ser Glu Cys Tyr Ser Asn Ser Glu
                580                 585                 590

Ala Arg Ala Phe Ala Leu Leu Val Arg Arg Asn Arg Cys Trp Ser Lys
            595                 600                 605

Thr Thr Cys Leu His Leu Ala Thr Glu Ala Asp Ala Lys Ala Phe Phe
610                 615                 620

Ala His Asp Gly Val Gln Ala Phe Leu Thr Arg Ile Trp Trp Gly Asp
625                 630                 635                 640

Met Ala Ala Gly Thr Pro Ile Leu Arg Leu Gly Ala Phe Leu Cys
                645                 650                 655

Pro Ala Leu Val Tyr Thr Asn Leu Ile Thr Phe Ser Glu Glu Ala Pro
                660                 665                 670

Leu Arg Thr Gly Leu Glu Asp Leu Gln Asp Leu Asp Ser Leu Asp Thr
            675                 680                 685

Glu Lys Ser Pro Leu Tyr Gly Leu Gln Ser Arg Val Glu Glu Leu Val
            690                 695                 700

Glu Ala Pro Arg Ala Gln Gly Asp Arg Gly Pro Arg Ala Val Phe Leu
705                 710                 715                 720

Leu Thr Arg Trp Arg Lys Phe Trp Gly Ala Pro Val Thr Val Phe Leu
                725                 730                 735

Gly Asn Val Val Met Tyr Phe Ala Phe Leu Phe Leu Phe Thr Tyr Val
                740                 745                 750

Leu Leu Val Asp Phe Arg Pro Pro Gln Gly Pro Ser Gly Pro Glu
            755                 760                 765

Val Thr Leu Tyr Phe Trp Val Phe Thr Leu Val Leu Glu Glu Ile Arg
            770                 775                 780

Gln Gly Phe Phe Thr Asp Glu Asp Thr His Leu Val Lys Lys Phe Thr
785                 790                 795                 800

Leu Tyr Val Gly Asp Asn Trp Asn Lys Cys Asp Met Val Ala Ile Phe
                805                 810                 815

Leu Phe Ile Val Gly Val Thr Cys Arg Met Leu Pro Ser Ala Phe Glu
                820                 825                 830

Ala Gly Arg Thr Val Leu Ala Met Asp Phe Met Val Phe Thr Leu Arg
            835                 840                 845

Leu Ile His Ile Phe Ala Ile His Lys Gln Leu Gly Pro Lys Ile Ile
            850                 855                 860

Val Val Glu Arg Met Met Lys Asp Val Phe Phe Phe Leu Phe Phe Leu
865                 870                 875                 880
```

Ser Val Trp Leu Val Ala Tyr Gly Val Thr Thr Gln Ala Leu Leu His
                885                 890                 895

Pro His Asp Gly Arg Leu Glu Trp Ile Phe Arg Arg Val Leu Tyr Arg
            900                 905                 910

Pro Tyr Leu Gln Ile Phe Gly Gln Ile Pro Leu Asp Glu Ile Asp Glu
        915                 920                 925

Ala Arg Val Asn Cys Ser Thr His Pro Leu Leu Glu Asp Ser Pro
    930                 935                 940

Ser Cys Pro Ser Leu Tyr Ala Asn Trp Leu Val Ile Leu Leu Val
945                 950                 955                 960

Thr Phe Leu Leu Val Thr Asn Val Leu Leu Met Asn Leu Leu Ile Ala
                965                 970                 975

Met Phe Ser Tyr Thr Phe Gln Val Val Gln Gly Asn Ala Asp Met Phe
            980                 985                 990

Trp Lys Phe Gln Arg Tyr Asn Leu Ile Val Glu Tyr His Glu Arg Pro
        995                 1000                1005

Ala Leu Ala Pro Pro Phe Ile Leu Leu Ser His Leu Ser Leu Thr
    1010                1015                1020

Leu Arg Arg Val Phe Lys Lys Glu Ala Glu His Lys Arg Glu His
    1025                1030                1035

Leu Glu Arg Asp Leu Pro Asp Pro Leu Asp Gln Lys Val Val Thr
    1040                1045                1050

Trp Glu Thr Val Gln Lys Glu Asn Phe Leu Ser Lys Met Glu Lys
    1055                1060                1065

Arg Arg Arg Asp Ser Glu Gly Glu Val Leu Arg Lys Thr Ala His
    1070                1075                1080

Arg Val Asp Phe Ile Ala Lys Tyr Leu Gly Gly Leu Arg Glu Gln
    1085                1090                1095

Glu Lys Arg Ile Lys Cys Leu Glu Ser Gln Ile Asn Tyr Cys Ser
    1100                1105                1110

Val Leu Val Ser Ser Val Ala Asp Val Leu Ala Gln Gly Gly Gly
    1115                1120                1125

Pro Arg Ser Ser Gln His Cys Gly Glu Gly Ser Gln Leu Val Ala
    1130                1135                1140

Ala Asp His Arg Gly Gly Leu Asp Gly Trp Glu Gln Pro Gly Ala
    1145                1150                1155

Gly Gln Pro Pro Ser Asp Thr
    1160                1165

<210> SEQ ID NO 3
<211> LENGTH: 36
<212> TYPE: DNA
<213> ORGANISM: Homo sapiens

<400> SEQUENCE: 3
aaaaaggtac cgccaccatg gtgagcaagg gcgagg                             36

<210> SEQ ID NO 4
<211> LENGTH: 32
<212> TYPE: DNA
<213> ORGANISM: Homo sapiens

<400> SEQUENCE: 4
aaaactcgag cccttgtaca gctcgtccat gc                                 32

METHODS OF SCREENING FOR TRPM5 MODULATORS

CROSS-REFERENCE

This application claims priority to U.S. provisional application Ser. No. 60/448,955, filed Feb. 21, 2003.

STATEMENT REGARDING FEDERALLY SPONSORED RESEARCH OR DEVELOPMENT

This invention was made with government support from NIH grants R01-GM065360, R01-NS040927 and R01 GM63954. The government has certain rights in the invention.

FIELD OF THE INVENTION

The present invention relates to the use of a novel family of differentiating Calcium-Activated Nonselective ("CAN") transmembrane channel polypeptides designated herein as "TRPM5".

BACKGROUND OF THE INVENTION

Ion channels are transmembrane multi-subunit proteins embedded in the cellular plasma membranes of living cells which permit the passage of specific ions from the extracellular side of the plasma membrane to the intracellular region of the cell. Specific ion transport is facilitated by a central aqueous pore which is capable of opening and closing due to changes in pore conformation. When the ion gate is open, ions flow freely through the channel. When the ion gate is closed, ions are prevented from permeating the channel. Ion channels are found in a multitude of multicellular eukaryotic species and in a myriad of different cell types. Ion channels may be either voltage-gated or ligand-gated. Channel gating is the process by which a particular channel is either open or closed. An ion channel may be capable of occupying a range of different "open" or "closed" states. The gating process may therefore require a particular sequence of transition states or inclusion of alternative transition states before a channel attains a particular level of gating. The gating process is modulated by a substance or agent, which in some way alters or affects the manner in which the channel opens or closes. A channel may be gated by a ligand such as a neurotransmitter, an internal primary or secondary messenger, or other bioactive agent. The ligand either attaches to one or more binding sites on the channel protein or attaches to a receptor that is associated with the channel. If the channel is voltage-gated, changes in the membrane potential trigger channel gating by conformational changes of charged elements within the channel protein. Whether a channel is ligand-gated or voltage-gated, a change in one part of the channel produces an effect in a different part of the channel which results in the opening or closing of a permeant pathway.

Transient receptor potential (TRP) proteins are a diverse family of proteins with structural features typical of ion channels. TRP proteins are expressed in a verity of organisms, tissues, and cell types, including electrically excitable and nonexcitable cells. The TRP channels have been divided into three main subfamilies: TRPC for "canonical", TRPM for "melastinin-like", and TRPV for "vanilloid-receptor-like".5 All TRP channels discovered thus far are composed of six putative transmembrane domains and a slightly hydrophobic pore-forming region. Both the N- and C-terminal domains of the TRP proteins are intracytoplasmic. Despite these similarities of structure, the functions of TRP channels are different from one channel to another, even amongst the members of the same subfamily.

The human TPRM subfamily currently consists of eight members. The activation mechanisms of several TPRM proteins have been elucidated and each has been shown to have specific ion selectivity and a particular mechanism of action.

SUMMARY OF THE INVENTION

The invention relates to use of a novel family of differentiating Calcium-Activated Nonselective ("CAN") transmembrane channel polypeptides designated herein as "TRPM5". The invention further relates to the use of recombinant nucleic acids that encode TRPM5. One aspect of the invention includes methods of determining binding of candidate bioactive agents to a TRPM5 polypeptide, for determining modulating of TRPM5 polypeptide activity, and for measuring TRPM5 channel permeability to monovalent cations. The invention further relates to methods of modulating the cellular expression of the nucleic acids that encode TRPM5 polypeptides.

One embodiment of the invention provides methods for screening for candidate bioactive agents that bind to a TRPM5 polypeptide. In this method, a TRPM5 polypeptide is contacted with a candidate agent, and it is determined whether the candidate agent binds to the TRPM5 polypeptide. An embodiment of the invention provides for contacting a TRPM5 polypeptide with a library of two or more candidate agents and then determining the binding of one or more of the candidate agents to TRPM5 polypeptide. In a preferred embodiment, the TRPM5 polypeptide comprises the amino acid sequence as set forth in SEQ ID NO:2 or the polypeptide encoded by the nucleic acid sequence set forth in SEQ ID NO:1.

In a further embodiment, the invention provides methods for screening for bioactive candidate agents that modulate the monovalent cationic permeability of a channel comprising a TRPM5 polypeptide. In this embodiment, the channel is contacted with a bioactive candidate agent, the channel is activated and the modulation of the monovalent cation permeability is detected. In some embodiments, the candidate agent(s) increase the monovalent cationic permeability of the TRPM5 channel. In other embodiments, the candidate agent(s) decrease the cationic permeability of the TRPM5 channel. In still other embodiments of the invention, the monovalent cations which permeate the TRPM5 channel include $Na^+$, $K^+$, and $Cs^+$. In a preferred embodiment, the channel is activated by increases in intracellular calcium concentration induced by calcium ionophores or calcium-mobilizing receptor agonists.

In a preferred embodiment, the candidate agent alters the membrane potential of the recombinant cell or cell-patch membrane comprising the channel by either increasing or decreasing monovalent cation permeability of the TRPM5 channel. The membrane potential can be measured, for example, by voltage measurements or with a membrane potential sensitive probe, such as bis-(1,3-dibutylbarbituric acid)trimethine oxonol (DiBAC4(3)) or a sodium specific probe such as sodium-binding benzofuran isophthalate (SBFI).

In a further embodiment, the channel comprising a TRPM5 polypeptide is in a recombinant cell which comprises a recombinant nucleic acid encoding a TRPM5 polypeptide and an inducible promoter operably linked or stably transfected under a constitutive promoter. The recombinant cell is induced to express the TRPM5 polypeptide and form a channel comprising the TRPM5 polypeptide. The cell is contacted with a bioactive candidate agent, the channel is activated and the modulation of the monovalent cation activity is detected. In a further embodiment, the cell is contacted with a monovalent cation indicator, preferably a fluorescent indicator. In this embodiment the intracellular levels of a monovalent cation are detected using the monovalent cation indicator specific for the cation. Examples of specific monovalent cation indicators include SBFI, specific for $Na^+$, or PBFI, specific for $K^+$.

In a preferred embodiment, the candidate agent alters the membrane potential of the recombinant cell by either increasing or decreasing monovalent cation permeability of the TRPM5 channel. The membrane potential can be measured, for example, by voltage measurements or with a membrane potential sensitive probe, such as bis-(1,3-dibutylbarbituric acid)trimethine oxonol (DiBAC4(3)).

It is another object of the invention to provide methods for measuring the monovalent ion permeability of a TRPM5 channel. In this method, a recombinant cell is provided, which comprises a recombinant nucleic acid encoding TRPM5 polypeptide, a promoter, either constitutive or inducible, preferably inducible, operably linked. The recombinant nucleic acid is expressed and a channel comprising the TRMP5 polypeptide is formed, the channel is activated and the monovalent cationic permeability of the channel is detected.

In one embodiment, the cell is contacted with a monovalent cation indicator, preferably a fluorescent indicator. In this embodiment the intracellular levels of a monovalent cation are detected using the monovalent cation indicator specific for the cation. Examples of specific monovalent cation indicators include SBFI, specific for $Na^+$, or PBFI, specific for $K^+$.

In a further embodiment, the cell is contacted with a bioactive candidate agent. In a preferred embodiment, the levels of monovalent cations are compared to endogenous levels in a cell in which recombinant TRPM5 is not expressed. In another embodiment, the cell may be any cell capable of being used with any recombinantly expressed channel protein for determining agents which modulate the activity of the channel. The expression of the recombinant channel is preferably under the control of an inducible promoter.

It is further an object of the invention to provide methods for screening for candidate bioactive agents that are capable of modulating expression of the TRPM5 polypeptide. In this method, a recombinant cell is provided which is capable of expressing a TRPM5 polypeptide. The recombinant cell is contacted with a candidate agent, and the effect of the candidate agent on TRPM5 polypeptide expression is determined. In some embodiments, the candidate agent may comprise a small molecule, protein, polypeptide, or nucleic acid (e.g., antisense nucleic acid). In another embodiment of the invention, TRPM5 polypeptide expression levels are determined in the presence of a candidate bioactive agent and these levels are compared to endogenous TRPM5 expression levels. Those candidate agents which regulate TRPM5 polypeptide expression can be tested in non-recombinant cells to determine if the same effect is reproduced.

The invention further provides for methods of verifying that a candidate bioactive agent is capable of binding to a TRPM5 polypeptide, modulating the monovalent cation permeability of a TRPM5 channel, or modulating expression of the TRPM5 polypeptide. One embodiment provides for providing a candidate bioactive agent previously identified as being capable of binding to a TRPM5 polypeptide, contacting a TRPM5 polypeptide with the candidate bioactive agent, and detecting whether the agent binds to the TRPM5 polypeptide.

Another embodiment provides for providing a candidate bioactive agent previously identified as being capable of modulating the monovalent cationic permeability of a TRPM5 channel, contacting a TRPM5 channel with the candidate bioactive agent, activating the TRPM5 channel, and detecting whether the agent modulates the monovalent cationic permeability of the TRPM5 channel. A further embodiment provides for providing a candidate bioactive agent previously identified as being capable of modulating the expression of a TRPM5 polypeptide, providing a recombinant cell capable of expressing a recombinant nucleic acid encoding a TRPM5 polypeptide, contacting the cell with a candidate bioactive agent and verifying the effect of the bioactive agent on the expression of the TRPM5 polypeptide.

BRIEF DESCRIPTION OF THE DRAWINGS

FIG. 1A depicts a Northern blot analysis of HEK-293 cells stably transfected with pcDNA3-TRPM5 and pcDNA3 alone. The blot was hybridized with $^{32}$P-labelled TRPM5 cDNA. To demonstrate equal loading of the single lanes, the blot was stripped after detection of the TRPM5 transcript and hybridized with $^{32}$P-labelled B-Actin cDNA.

FIG. 1B depicts confocal laser microscopic analysis of HEK-293 cells expressing a EGFP-TRPM5 fusion protein. The 3D distribution of EGFP-TRPM5 demonstrates that significant amounts of the protein is localized to the outer cell membrane.

FIG. 1C depicts the average development of TRPM5 inward and outward currents in HEK-293 cells perfused with 500 nM $[Ca^{2+}]i$ (n=5). Currents were measured at −80 mV or +80 mV, respectively.

FIG. 1D depicts a typical I/V curve of TRPM5 currents measured 5 s or 40 s after establishment of whole-cell configuration with 500 nM $[Ca^{2+}]i$.

FIG. 1E depicts a concentration-response curve of TRPM5 currents (left axis, filled circles; n=5-20). The fit to the rising phase yields an apparent EC50 of 850 nM (Hill coefficient 4), the IC50 of the inhibitory phase was 1.1 µM (Hill coefficient 6). The right axis shows the dose-dependence of TRPM4 currents evoked by different concentrations of intracellular [Ca2+]i (data re-calculated by WebmaxC, see Methods). The fit to these data yields an EC50 of 885 nM (Hill coefficient 3.6).

FIG. 2A depicts the average currents of TRPM5 overexpressing HEK-293 cells perfused with 500 nM $[Ca^{2+}]i$ and superfused with isotonic $CaCl_2$ (120 mM) at the time indicated by the bar (n=3). During application, inward currents were suppressed and outward currents increased. Data were not leak-subtracted.

FIG. 2B depicts a typical I/V curve before (thin line) and at the end of isotonic $Ca^{2+}$ application (thick line). The inset demonstrates the shift in reversal potential to negative values.

FIG. 2C depicts the application of divalent-free NaCl-based extracellular solution (DVF) with 1 mM Na-EDTA and 20 U/ml thrombin to activate TRPM5 as indicated by the bar (n=5).

FIG. 2D depicts a typical I/V curve during DVF application.

FIG. 3A depicts the average currents measured at −80 mV and +80 mV, respectively (n=5). The bar indicates the application of thrombin (20 U/ml).

FIG. 3B depicts the average $[Ca^{2+}]i$ signals in response to thrombin application, same cells as in FIG. 3A (n=5).

FIG. 3C depicts the average outward currents taken from FIG. 3A and superimposed on the differentiated average calcium signal (right axis). Note that the activation of the channels occurs in parallel with the rate of change in $[Ca^{2+}]i$.

FIG. 3D depicts a leak-subtracted I/V curve from FIG. 3A and 96 s after whole cell establishment, measured during thrombin application.

FIG. 3E depicts a typical example (n=9 cells) of currents at −80 mV and +80 mV evoked by 50 μM cyclopiazonic acid. The arrow points to a burst of endogenous TRPM4 activity (sample I/V in inset panel).

FIG. 3F depicts the corresponding fura-2 measurements of the same cell as shown in FIG. 3E. The bar indicates CPA application.

FIG. 4A depicts studies in which the inside-out patches were pulled from HEK-293 cells stably expressing TRPM5 channels. To record single channels a ramp protocol of 4.5 s from −100 mV to +100 mV was given with no wait time in between ramps. Ramps that had no channel activity during $Ca^{2+}$ application ere used for leak correction. Data were acquired at 2.9 kHz filter setting and digitally filtered at 50 Hz for display purposes. The top panel shows the time of excision of the patch into 0 $Ca^{2+}$ solution, the three middle panels are consecutive examples of data acquired during exposure of the patch to 300 nM $Ca^{2+}$. The last panel is an example 1 s after stop of application and removal of $Ca^{2+}$. This patch had at least 7 channels. The dashed lines indicate the extrapolation of single-channel currents through individual one channel starting at the reversal potential for TRPM5 (0 mV) and ending at either −100 mV or +100 mV. The slope for positive potentials gives a channel conductance of 28 pS, the slope for the inward currents is 23 pS. Records are representative of all 5 patches recorded this way. In control cells (WT HEK-293 not expressing TRPM5), 3 out of 7 patches had no ion channel activity during $Ca^{2+}$ application, 3 patches had up to 3 TRPM4-like channels and one patch contained a $Ca^{2+}$-activated $Cl^−$ channel.

FIG. 4B depicts an ensemble I/V curve of TRPM5 single channels (75 ramps) and recordings made in WT HEK-293 cells (control, 98 ramps) during 300 nM $Ca^{2+}$ exposure and collected by 4.5 s ramps.

FIG. 4C depicts the Current-Voltage relationship of TRPM5 single channels. Each point was calculated measuring 15-25 events per voltage from 5 patches, averaged and plotted as current versus voltage (+S.E.M.).

FIG. 4D depicts the average charge measured before during and after exposure of TRPM5 expressing patches to 300 nM Ca2+ (same patches as in A, B and C, n=5), assessed by integrating ramp currents between 0 mV and +100 mV.

FIG. 5A depicts total RNA from different human and murine cell lines was isolated as described and transcribed into cDNA. RT PCR was performed with species-specific primers for the TRPM4/Trpm4 and the TRPM5/Trpm5 genes. Products were isolated and sequenced. As control for non RT-based PCR products a RT protocol without reverse transcriptase was performed. Equal amounts of cDNA were used as demonstrated with the β-Actin product amounts. cDNA from the human cell lines Ramos and Hela and the murine cell lines Min, A20 and Cath.A contain TRPM5/Trpm5 transcripts. TRPM4/Trpm4 cDNA products were found in human Hela, Jurkat and Wt128 cell lines and in all three murine cell lines.

FIG. 5B depicts endogenous Trpm5 expression in cultured pancreatic beta (INS-1) cells. Total RNA from the INS-1 cell line was isolated as described and transcribed into cDNA. RT PCR was performed with rodent specific primers for the Trpm5 gene. The product was isolated and sequenced. As control for non RT-based PCR products, a RT protocol without reverse transcriptase was performed. cDNA from the rat INS-1 cell line contains endogenous Trpm5 transcripts.

FIG. 5C depicts the development of whole-cell currents measured in a typical INS-1 cell (n=8) perfused with 800 nM $[Ca^{2+}]i$ and measured at −80 mV and +80 m, respectively. Since the delay of TRPM5 activation varied between cells (26 s to 109 s) an example is shown instead of averages (average delay at 500 nM $[Ca^{2+}]i$=63±11 (n=3) and at 800 nM=53±10 s (n=8) with no statistical significance). In all cases, TRPM5-like currents activate and inactivate completely. The initial drop of currents seen after break-in is due to the inactivation of DRK channels at the holding potential (0 mV). Data were leak-corrected by subtracting the 12th ramp (24 s after whole-cell establishment) from all previous and subsequent ramps.

FIG. 5D depicts the average raw data traces of TRPM5-like currents (n=8) extracted at the peak. Data were leak-corrected by subtracting an appropriate control ramp before current development. The leak-corrected reversal potential was −17 mV±1 mV (n=8), slightly more negative than in the expression system (−5 mV), presumably to some small contaminating $K^+$ and/or $Cl^−$ currents.

FIG. 5E depicts a dose-response curve of endogenous TRPM5-like currents in INS-1 cells. Note that neither 100 nM (n=3) nor 300 nM (n=3) activated any currents. At 500 nM (n=3) and 800 nM (n=8) a distinctive, transient TRPM5-like current was activated. 1 μM $[Ca^{2+}]i$ caused large additional $Ca^{2+}$-activated currents (n=6, data not shown), which prevented accurate assessment of TRPM5 in isolation.

FIG. 6 depicts the nucleic acid molecule of a TRPM5 cDNA comprised of nucleic acid sequences from 1 through about 3913 (SEQ ID NO: 1).

FIG. 7 shows the amino acid sequence of a human TRPM5 polypeptide comprised of sequences from 1 through about 1165 (SEQ ID NO:2).

DETAILED DESCRIPTION

Figure 1:
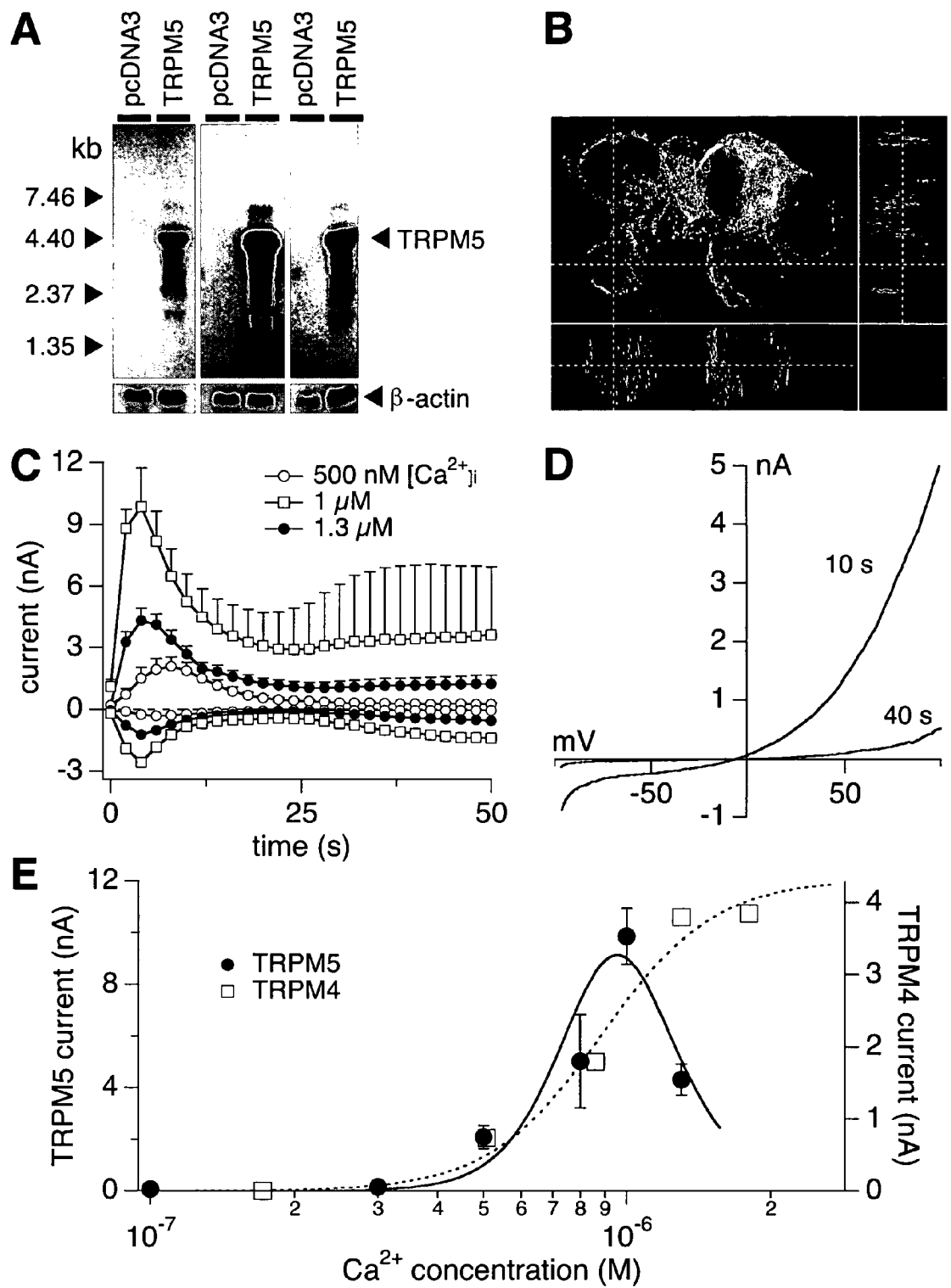
FIGS. 1A-E depict studies showing that TRPM5 is a transmembrane protein and a calcium-activated cation channel.

The invention relates, in part, to methods useful in identifying molecules that bind to TRPM5 polypeptides, which modulate TRPM5 ion channel activity, and which alter expression of TRPM5 polypeptides within cells. The TRPM5 channels as described herein comprise TRPM5 polypeptides, also referred to TRPM5 proteins, which are in turn encoded by TRPM5 nucleic acids. The ion channels described herein are preferably formed in a human embryonic kidney cell line, such as HEK-293 cells, and comprise one or more novel TRPM5 polypeptides, which exhibit one or more of the unique TRPM5 properties described herein.

TRPM5 is activated by a rapid increase in intracellular $Ca^{2+}$ levels (Prawitt D, et al, "TRPM5 is a transient Ca2+-activated cation channel responding to rapid changes in [Ca2+]I", *Proc Natl Acad Sci USA.* 100(25):15166-71 (2003) hereby incorporated by reference).

The increase in intracellular $Ca^{2+}$ levels can be induced by the presence of inositol 1,4,5-trisphosphate (InsP3)-producing receptor agonists, calcium ionophores, or by any other means that induce rapid $Ca^{2+}$ changes.

As described herein, the term "TRPM5" refers to a member of the novel family of $Ca^{2+}$ regulated transmembrane channel polypeptides. The polypeptides are also defined by their amino acid sequence, the nucleic acids which encode them, and the novel properties of TRPM5. Such novel properties include specific activation by a fast increase in cytoplasmic $Ca^{2+}$ levels, direct gating by $Ca^{2+}$, conduction of monovalent cations such as $Na^+$, $K^+$, and $Cs^+$ without significant $Ca^{2+}$ permeation, regulation of $Ca^{2+}$-influxes by modulation of membrane potential, and an absence of $Ca^{2+}$-independent inactivation.

The sequence for a TRPM5 polypeptide disclosed herein as SEQ ID NO: 2 (FIG. 7) was derived from human kidney cells. However, TRPM5 is broadly expressed in various mammalian tissues (for example, in human (NCBI accession number NM014555), in mouse (NCBI accession numbers AB039952, AF228681, AY280364, AY280365, NM020277), and in chimpanzee (NCBI accession number ABAY401206.

TRPM5 is expressed as a 4.5-kb transcript in a variety of fetal and adult human tissue including taste receptor cells, neuronal cells (Cath.A), Burkitt lymphoma cells (Ramos), as well as fibroblasts (A20), epithelial cervical cancer-derived cells (Hela) and pancreatic beta cells (Min) (FIG. 5A) (Prawitt, D. et al., *Hum. Mol. Genet.* 9, 203-16 (2000); Perez, et al., *Nat. Neurosci.*, 5: 1169-1176 (2002), Zhang, et al., *Cell*, 112: 293-301 (2003); Enklaar, T. et al., *Genomics* 67,179-87 (2000), all of which are hereby incorporated by reference).

The presence of TRPM5 in a variety of tissues indicates a generalized role of the channel as a tool that couples agonist-induced intracellular Ca 2+ release to electrical activity and subsequent cellular responses.

The finding that TRPM5 is present in pancreatic beta cells, where changes in $[Ca^{2+}]i$ are coupled with electrical activity, implicates TRPM5 in the release of insulin. Additional support for the implication of TRPM5 in the cellular function of insulin release comes from Goto-Kakizaki (GK) rats, which are a genetic model for non-obese type-2 diabetes. Adult GK rats show decreased beta cell mass, impaired insulin secretion and mild hyperglycemia and have been reported to posses strongly reduced levels of TRPM5 (Irminger, J. et al. 38th EASD *Annual Meeting* Abstract #444 (2002)), consistent with a critical role of TRPM5 in this cell type. The $Ca^{2+}$ sensing properties of TRPM5 are ideally suited to produce a transient depolarizing stimulus and may contribute to both initial triggering of electrical activity as well as to the oscillatory changes in electrical activity in the above cellular contexts as well as in other cells that express the protein.

The TRPM5 gene was identified during functional analysis of the chromosomal region (I 1p15.5) associated with loss of heterozygosity in a variety of childhood and adult tumors and the Beckwith-Wiedemann-Syndrome (Prawitt, D. et al., *Hum. Mol. Genet.* 9, 203-16 (2000)).

Topology programs predict that full-length TRPM5 polypeptide is a transmembrane protein that contains six transmembrane domains, a finding that is validated by confocal laser microscopic analysis (FIG. 1B).

The TRPM5 channel is directly activated by elevated $[Ca^{2+}]i$ both in whole-cell and excised membrane patches. TRPM5 is characterized by a single-channel conductance of 25 pS and is specific for monovalent cations, being essentially impermeable to $Ca^{2+}$. It therefore shares the activation mechanism as well as selectivity with the $Ca^{2+}$-activated cation channel TRPM4 (Launay, P. et al., *Cell* 109, 397-407 (2002)), but unlike TRPM4, it is strongly activated by intracellular receptor-mediated $Ca^{2+}$ release, resulting in a transient activation that depends on the rate of change in $[Ca^{2+}]i$ rather than its absolute concentration. TRPM5 is referred to as differentiating CAN because it responds to the rate of $[Ca^{2+}]i$ change rather than absolute levels of $[Ca^{2+}]i$.

The magnitude of TRPM5 currents is dependent on the level of $[Ca^{2+}]i$, which triggers increases in channel activity up to 1 μM, but then becomes inhibitory, resulting in a bell-shaped dose-response curve (FIG. 1E). Another feature of TRPM5 is the pronounced and rapid inactivation of TRPM5 currents observed at all $Ca^{2+}$ concentrations, suggesting that it is not directly mediated by $Ca^{2+}$, but rather represents an intrinsic property of TRPM5 or alternatively is caused by a regulatory mechanism. The transient nature of these currents is a distinctive feature of TRPM5, setting it apart from the persistent activation of TRPM4. Additionally, TRPM4 is relatively unresponsive to short $Ca^{2+}$-release transients and requires $Ca^{2+}$ influx to fully activate (Launay, P. et al., *Cell* 109, 397-407 (2002)).

TRPM5 can be derived from natural sources or recombinantly modified to make TRPM5 variants. The term "TRPM5 sequence" specifically encompasses naturally-occurring truncated or secreted forms (e.g., an extracellular domain sequence or an amino-terminal fragment), naturally-occurring variant forms (e.g., alternatively spliced forms) and naturally-occurring allelic variants. The native sequence of the TRPM5 polypeptide from human kidney cells is a full-length or mature native sequence TRPM5 polypeptide comprising amino acids from 1 through about 1165 of SEQ ID NO:2 (FIG. 7).

The TRPM5 polypeptide that may be used in the methods of the invention or for other purposes includes polypeptides having at least about 80% amino acid sequence identity, more preferably at least about 85% amino acid sequence identity, even more preferably at least about 90% amino acid sequence identity, and even more preferably at least about 95%, 97%, 98% or 99% sequence identity with the amino acid sequence of SEQ ID NO:2 or fragments thereof. Such TRPM5 polypeptides include, for instance, TRPM5 polypeptides wherein one or more amino acid residues are substituted and/or deleted, at the N- or C-terminus, as well as within one or more internal domains, of the sequence of SEQ ID NO:2. Those skilled in the art will appreciate that amino acid changes may alter post-translational processes of the TRPM5 polypeptide variant, such as changing the number or position of glycosylation sites or altering the membrane anchoring characteristics. All TRPM5 polypeptides, however, exhibit one or more of the novel properties of the TRPM5 polypeptides as defined herein.

"Percent (%) amino acid sequence identity" with respect to the TRPM5 polypeptide sequences identified herein is defined as the percentage of amino acid residues in a candidate sequence that are identical with the amino acid residues of SEQ ID NO:2 (FIG. 7), after aligning the sequences and introducing gaps, if necessary, to achieve the maximum percent sequence identity, and not considering any conservative substitutions as part of the sequence identity. The % identity values may be generated by WU-BLAST-2 (Altschul et al., *Methods in Enzymology*, 266:460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a further embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In yet another embodiment, TRPM5 polypeptides from humans or from other organisms may be identified and isolated using oligonucleotide probes or degenerate polymerase chain reaction (PCR) primer sequences with an appropriate genomic or cDNA library. As will be appreciated by those in the art, the TRPM5 unique nucleic acid sequence comprising nucleotide sequences of SEQ ID NO:1 (FIG. 6) encoding amino acids 1-1165 of SEQ ID NO:2 (FIG. 7) or portions thereof, is particularly useful as a probe or PCR primer sequence. As is generally known in the art, preferred PCR primers are from about 15 to about 35 nucleotides in length, with from about 20 to about 30 being preferred, and may contain inosine as needed. The conditions for the PCR reaction are well known in the art.

In a preferred embodiment, TRPM5 is a "recombinant protein" or "recombinant polypeptide" which is made using recombinant techniques, i.e. through the expression of a recombinant TRPM5 nucleic acid. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, with at least about 90% being more preferred and at least about 95% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or of amino acid substitutions, additions and deletions, as discussed below.

In a further embodiment, TRPM5 variants may be recombinantly engineered by replacing one amino acid with another amino acid having similar structural and/or chemical properties, such as the replacement of a leucine with a serine, i.e., conservative amino acid replacements.

In a further embodiment substitutions, deletions, additions or any combination thereof may be used to make TRPM5 variants. Generally these changes are done on a few amino acids to minimize the alteration of the molecule. However, larger changes may be tolerated in certain circumstances. When small alterations in the characteristics of the TRPM5 polypeptide are desired, substitutions are generally made in accordance with the following Table 1:

TABLE 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In a further embodiment, substantial changes in function or in immunological identity are made by selecting substitutions that are less conservative than those shown in Table 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. The TRPM5 variants of this embodiment exhibit one or more properties of the TRPM5 polypeptides originally defined herein.

In a further embodiment, the variants typically exhibit the same qualitative biological activity and will elicit the same immune response as the naturally-occurring analogue, although variants also are selected to modify the characteristics of the TRPM5 polypeptides as needed. Alternatively, the variant may be designed such that the biological activity of the TRPM5 polypeptides is altered. For example, glycosylation sites may be altered or removed.

The polypeptides encoded by nucleic acid variants exhibit at least one of the novel TRPM5 polypeptide properties defined herein.

As used herein, "TRPM5 nucleic acids" or their grammatical equivalents, refer to nucleic acids, that encode TRPM5 polypeptides exhibiting one or more of the novel TRPM5 polypeptide properties previously described. The TRPM5 nucleic acids exhibit sequence homology to SEQ ID NO:1 (FIG. 6) where homology is determined by comparing sequences or by hybridization assays.

A TRPM5 nucleic acid encoding a TRPM5 polypeptide is homologous to the cDNA forth in FIG. 6 (SEQ ID NO:1).

Such TRPM5 nucleic acids are preferably greater than about 75% homologous, more preferably greater than about 80%, more preferably greater than about 85% and most preferably greater than about 90% homologous. In some embodiments the homology will be as high as about 93%, 95%, 97%, 98% or 99%. Homology in this context means sequence similarity or identity, with identity being preferred. A preferred comparison for homology purposes is to compare the sequence containing sequencing differences to the known TRPM5 sequence. This homology will be determined using standard techniques known in the art, including, but not limited to, the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection.

In a preferred embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In preferred embodiment, a BLAST algorithm is used. BLAST is described in Altschul et al., *J. Mol. Biol.* 215:403-410, (1990) and Karlin et al., *PNAS USA* 90:5873-5787 (1993). A particularly useful BLAST program is the WU-BLAST-2, obtained from Altschul et al., *Methods in Enzymology*, 266:460-480 (1996); http://blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a preferred embodiment, "percent (%) nucleic acid sequence identity" is defined as the percentage of nucleotide residues in a candidate sequence that are identical with the nucleotide residue sequences of SEQ ID NO:1 (FIG. 6). A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of SEQ ID NO:1 (FIG. 6), it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

As described above, the TRPM5 nucleic acids can also be defined by homology as determined through hybridization studies. Hybridization is measured under low stringency conditions, more preferably under moderate stringency conditions, and most preferably, under high stringency conditions. The proteins encoded by such homologous nucleic acids exhibit at least one of the novel TRPM5 polypeptide properties defined herein. Thus, for example, nucleic acids which hybridize under high stringency to a nucleic acid having the sequence set forth as SEQ ID NO:1 (FIG. 6) and their complements, are considered TRPM5 nucleic acid sequences providing they encode a protein having a TRPM5 property.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional examples of stringency of hybridization reactions, see Ausubel et al., *Current Protocols in Molecular Biology*, Wiley Interscience Publishers, (1995), hereby incorporated by reference in its entirety.

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions may be used, as are known in the art. For additional details regarding stringency of hybridization reactions, see Ausubel et al., *Current Protocols in Molecular Biology*, Wiley Interscience Publishers, (1995).

The TRPM5 nucleic acids, as defined herein, may be single stranded or double stranded, as specified, or contain portions of both double stranded or single stranded sequence. As will be appreciated by those in the art, the depiction of a single strand also defines the sequence of the other strand; thus the sequences described herein also include the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The TRPM5 nucleic acids, as defined herein, are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Homologs and alleles of the TRPM5 nucleic acid molecules are included in the definition.

The recombinant cDNA nucleic acid (SEQ ID NO: 1) encoding a TRPM5 protein (SEQ ID NO:2), or portions thereof, may be used as hybridization probes for a cDNA library to isolate the full-length TRPM5 gene from other multicellular eukaryotic species, or to isolate still other genes (for instance, those encoding naturally-occurring variants of the TRPM5 polypeptide or the TRPM5 polypeptide from other multicellular eukaryotic species) which have a desired sequence identity to a particular TRPM5 nucleotide coding sequence. Optionally, the length of the probes will be about 20 through about 50 bases. The hybridization probes may be derived from the nucleotide sequences of SEQ ID NO:1 or from genomic sequences including promoters, enhancer elements and introns of particular native nucleotide sequences of TRPM5. By way of example, a screening method will comprise isolating the coding region of a TRPM5 gene using the known DNA sequence to synthesize a selected probe of about 40 bases.

Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TRPM5 gene of the invention can be used to screen libraries of human cDNA, genomic DNA or mRNA to determine which members of such libraries the probe hybridizes to. Hybridization have been previously described below.

The probes may also be employed in PCR techniques to generate a pool of sequences for identification of closely related TRPM5 nucleotide coding sequences. Nucleotide sequences encoding TRPM5 polypeptides can also be used to construct hybridization probes for mapping the gene which encodes that TRPM5 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries In another embodiment, DNA encoding the TRPM5 polypeptide may be obtained from a cDNA library prepared from tissue believed to possess the TRPM5 mRNA and to express it at a detectable level. Accordingly, human TRPM5 DNA can be conveniently obtained from a cDNA library prepared from human tissue, or a cDNA kidney library prepared from human kidney tissue. The TRPM5-encoding gene may also be obtained from a multicellular eukaryotic genomic library or by oligonucleotide synthesis.

Libraries can be screened with probes (such as antibodies to TRPM5 DNA or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989) hereby incorporated by reference in its entirety. An alternative means to isolate the gene encoding TRPM5 is to use PCR methodology [Sambrook et al., supra; Dieffenbach et al., *PCR Primer: A Laboratory Manual* (Cold Spring Harbor Laboratory Press, 1995) )hereby incorporated by reference in its entirety].

The examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ADPR, biotinylation or enzyme labeling. Hybridization conditions, including moderate stringency and high stringency, are provided in Sambrook et al., supra, and have been described previously.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, BLAST, BLAST2 and INHERIT which employ various algorithms to measure homology, as has been previously described.

Nucleic acid encoding TRPM5 polypeptides, as defined herein, may be obtained by screening selected cDNA or genomic libraries using all or part of the nucleotide sequences of SEQ ID NO:1 (FIG. 6). Conventional primer extension procedures as described in Sambrook et al., supra, are used to detect precursors and processing intermediates of mRNA that may not have been reverse-transcribed into cDNA.

Nucleotide sequences (or their complement) encoding the TRPM5 polypeptides have various applications in the art of molecular biology, including uses as hybridization probes, in chromosome and gene mapping, and in the generation of anti-sense RNA and DNA.

In another embodiment, the TRPM5 nucleic acids, as defined herein, are useful in a variety of applications, including diagnostic applications, which will detect naturally occurring TRPM5 nucleic acids, as well as screening applications; for example, biochips comprising nucleic acid probes to the TRPM5 nucleic acids sequences can be generated. In the broadest sense, then, by "nucleic acid" or "oligonucleotide" or grammatical equivalents herein means at least two nucleotides covalently linked together.

In another embodiment, the TRPM5 nucleic acid sequence of SEQ ID NO:1 (FIG. 6), as described above, is a cDNA fragment of a larger gene, i.e. it is a nucleic acid segment. "Genes" in this context include coding regions, non-coding regions, and mixtures of coding and non-coding regions. Accordingly, as will be appreciated by those in the art, using the sequences provided herein, additional sequences of TRPM5 genes can be obtained, using techniques well known in the art for cloning either longer sequences or the full length sequences; see Maniatis et al., and Ausubel, et al., supra, hereby expressly incorporated by reference.

Once the TRPM5 nucleic acid, as described above, is identified, it can be cloned and, if necessary, its constituent parts recombined to form the entire TRPM5 gene. Once isolated from its natural source, e.g., contained within a plasmid or other vector or excised therefrom as a linear nucleic acid segment, the recombinant TRPM5 nucleic acid can be further-used as a probe to identify and isolate other TRPM5 nucleic acids, from other multicellular eukaryotic organisms, for example additional coding regions. It can also be used as a "precursor" nucleic acid to make modified or variant TRPM5 nucleic acids.

In another embodiment, the TRPM5 nucleic acid (e.g., cDNA or genomic DNA), as described above, encoding the TRPM5 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A host cell comprising such a vector is also provided. By way of example, the host cells may be mammalian host cell lines which include Chinese hamster ovary (CHO), COS cells, cells isolated from human bone marrow, human spleen or kidney cells, cells isolated from human cardiac tissue, human pancreatic cells, and human leukocyte and monocyte cells. More specific examples of host cells include monkey kidney CV1 line transformed by SV40 (COS-7, ATCC CRL 1651); human embryonic kidney line (293 or 293 cells subcloned for growth in suspension culture, Graham et al., *J. Gen. Virol.*, 36:59 (1977)); Chinese hamster ovary cells/-DHFR (CHO, Urlaub and Chasin, *Proc. Natl. Acad. Sci. USA*, 77:4216 (1980)); human pancreatic β-cells; mouse sertoli cells (TM4, Mather, *Biol. Reprod.*, 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art. In the preferred embodiment, HEK-293 cells are used as host cells. A process for producing TRPM5 polypeptides is further provided and comprises culturing host cells under conditions suitable for expression of the TRPM5 polypeptide and recovering the TRPM5 polypeptide from the cell culture.

Once expressed in host cell, the TRPM5 polypeptides are capable of forming TRPM5 channels comprised of at least one TRPM5 polypeptide.

In another embodiment, expression and cloning vectors are used which usually contain a promoter, either constitutive or inducible, that is operably linked to the TRPM5-encoding nucleic acid sequence to direct mRNA synthesis. Promoters recognized by a variety of potential host cells are well known. The transcription of a TRPM5 DNA encoding vector in mammalian host cells is preferably controlled by an inducible promoter, for example, by promoters obtained from heterologous mammalian promoters, e.g., the actin promoter or an immunoglobulin promoter, and from heat-shock promoters. Examples of inducible promoters which can be practiced in the invention include the hsp 70 promoter, used in either single or binary systems and induced by heat shock; the metallothionein promoter, induced by either copper or cadmium (Bonneton et al., FEBS Lett. 1996 380(1-2): 33-38); the *Drosophila opsin* promoter, induced by *Drosophila retinoids* (Picking, et al., Experimental Eye Research. 1997 65(5): 717-27); and the tetracycline-inducible full CMV promoter. Of all the promoters identified, the tetracycline-inducible full CMV promoter is the most preferred. Examples of constitutive promoters include the GAL4 enhancer trap lines in which expression is controlled by specific promoters and enhancers or by local position effects; and the transactivator-responsive promoter, derived from *E. coli*, which may be either constitutive or induced, depending on the type of promoter it is operably linked to.

Transcription of a DNA encoding the TRPM5 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the TRPM5 coding sequence, but is preferably located at a site 5' from the promoter.

The methods of the invention utilize TRPM5 polypeptides or nucleic acids which encode TRPM5 polypeptides for identifying candidate bioactive agents which bind to TRPM5, which modulate the activity of TRPM5 ion channels, or which alter the expression of TRPM5 within cells.

One embodiment of the invention provides for a method of screening for a candidate bioactive agent capable of binding to TRPM5. In a preferred embodiment for binding assays, either TRPM5 or the candidate bioactive agent is labeled with, for example, a fluorescent, a chemiluminescent, a chemical, or a radioactive signal, to provide a means of detecting the binding of the candidate agent to TRPM5. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound TRPM5. As known in the art, unbound labeled streptavidin is removed prior to analysis. Alternatively, TRPM5 can be immobilized or covalently attached to a surface and contacted with a labeled candidate bioactive agent. Alternatively, a library of candidate bioactive agents can be immobilized or covalently attached to a biochip and contacted with a labeled TRPM5. Procedures that may also be used employ biochips and are well known in the art.

The term "candidate bioactive agent" as used herein describes any molecule which binds to TRPM5, modulates the activity of a TRPM5 ion channel, or alters the expression of TRPM5 within cells. A molecule, as described herein, can be an oligopeptide, small organic molecule, polysaccharide, polynucleotide, or multivalent cation etc. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are multivalent cations or organic molecules, or small organic compounds having a molecular weight of more than 100 and less than about 2,500 daltons (D). Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Candidate agents may be bioactive agents that are known to bind to ion channel proteins or known to modulate the activity of ion channel proteins, or alter the expression of ion channel proteins within cells. Candidate agents may also be bioactive agents that were not previously known to bind to ion channel proteins or known to modulate the activity of ion channel proteins, or alter the expression of ion channel proteins within cells.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes amino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of multicellular eucaryotic proteins may be made for screening in the methods of the invention. Particularly preferred in this embodiment are libraries of multicellular eukaryotic proteins, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, anti-sense RNAs and DNAs can be used as therapeutic agents for blocking the expression of certain TRPM5 genes in vivo. It has already been shown that short antisense oligonucleotides can be imported into cells where they act as inhibitors, despite their low intracellular concentrations caused by their restricted uptake by the cell membrane. (Zamecnik et al., (1986), *Proc. Natl. Acad. Sci. USA* 83:4143-4146). The anti-sense oligonucleotides can be modified to enhance their uptake, e.g. by substituting their negatively charged phosphodiester groups by uncharged groups. In a preferred embodiment, TRPM5 anti-sense RNAs and DNAs can be used to prevent TRPM5 gene transcription into mRNAs, to inhibit translation of TRPM5 mRNAs into proteins, and to block activities of preexisting TRPM5 proteins.

Another embodiment provides for methods of screening for candidate bioactive agents that modulate the monovalent cationic permeability of the TRPM5 channel. Modulation of the monovalent cationic permeability of the TRPM5 channel can, for example, be determined by measuring the inward and outward currents in whole cell patch clamp assays or single-channel membrane patch assays in the presence and absence of the candidate bioactive agent. In an alternative embodiment, the modulation of monovalent cation activity is monitored as a function of monovalent cation currents and/or membrane-potential of a cell comprising a TRPM5 channel. For example, the modulation of membrane potential is detected with the use of a membrane potential-sensitive probe. In a preferred embodiment, the membrane potential sensitive probe is a fluorescent probe such as bis-(1,3-dibutylbarbituric acid)trimethine oxonol (DiBAC4(3)) (*Handbook of Fluorescent Probes and Research Chemicals*, 9th ed. Molecular Probes, incorporated herein by reference). The use of a fluorescent membrane potential-sensitive probe allows rapid detection of change in membrane potential by monitoring change in fluorescence with the use of such methods as fluorescence microscopy, flow cytometry and fluorescence spectroscopy, including use of high through-put screening methods utilizing fluorescence detection (Alvarez-Barrientos, et al., "Applications of Flow Cytometry to Clinical Microbiology", *Clinical Microbiology Reviews*, 13(2): 167-195, (2000)).

Modulation of the monovalent cationic permeability of the TRPM5 channel by a candidate agent can be determined by contacting a cell that expresses TRMP5 with a monovalent cation and a monovalent cation indicator which reacts with the monovalent cation to generate a signal. The intracellular levels of the monovalent cation are measured by detecting the indicator signal in the presence and absence of a candidate bioactive agent. Another embodiment provides for comparing the intracellular monovalent cation levels in cells that express TRPM5 with cells that do not express TRPM5 in the presence and absence of a candidate bioactive agent.

As used herein, a monovalent cation indicator is a molecule that is readily permeable to a cell membrane or otherwise amenable to transport into a cell e.g., via liposomes, etc., and upon entering a cell, exhibits a fluorescence signal, or other detectable signal, that is either enhanced or quenched upon contact with a monovalent cation. Examples of monovalent cation indicators useful in the invention are set out in Haugland, R. P. *Handbook of Fluorescent Probes and Research Chemicals.*, 9th ed. Molecular Probes, Inc Eugene, Oreg., (2001) incorporated herein by reference in its entirety.

In a preferred embodiment, the monovalent cation indicator is a sodium indicator. Examples of sodium indicators include SBFI, CoroNa Green, CoroNa Red, and Sodium Green (*Handbook of Fluorescent Probes and Research Chemicals*, 9th ed. Molecular Probes). In a further preferred embodiment, the monovalent cation indicator is a potassium indicator, such as PBFI (*Handbook of Fluorescent Probes and Research Chemicals*, 9th ed. Molecular Probes).

The levels of intracellular $Ca^{2+}$ levels are detectable using indicators specific for $Ca^{2+}$. Indicators that are specific for $Ca^{2+}$ include fura-2, indo-1, rhod-2, fura-4F, fura-5F, fura-6F and fura-FF, fluo-3, fluo-4, Oregon Green 488 BAPTA, Calcium Green, X-rhod-1 and fura-red (*Handbook of Fluorescent Probes and Research Chemicals*, 9th ed. Molecular Probes).

In a further preferred embodiment, both the levels of intracellular $Ca^{2+}$ and the influx of monovalent cations into the cell are measured simultaneously. In this embodiment, a $Ca^{2+}$ specific indicator is used to detect levels of $Ca^{2+}$ and a monovalent cation specific indicator is used to detect levels of monovalent cation. The $Ca^{2+}$ indicator and the monovalent cation specific indicator are chosen such that the signals from the indicators are capable of being detected simultaneously. For example, both indicators have a fluorescent signal but the excitation and/or emission spectra of both indicators are distinct such that the signal from each indicator can be detected at the same time.

In yet a further preferred embodiment, both the levels of intracellular $Ca^{2+}$ and the change in membrane potential are measured simultaneously. In this embodiment a $Ca^{2+}$ specific indicator is used to detect levels of $Ca^{2+}$ and a membrane potential sensitive probe is used to detect changes in the membrane potential. The $Ca^{2+}$ indicator and the membrane potential sensitive probe are chosen such that the signals from the indictors and probes are capable of being detected simultaneously. For example, both the indicator and probe have a fluorescent signal but the excitation and/or emission spectra of both indicators is distinct such that the signal from each indicator can be detected at the same time.

Before modulation of the TRPM5 channel can be measured, TRPM5 must be activated by a rapid increase in intracellular $Ca^{2+}$ levels to allow the flow of monovalent cations across the membrane. The increase in intracellular $Ca^{2+}$ levels can be induced by the presence of a calcium ionophore, thrombin, inositol 1,4,5-trisphosphate (InsP3)-producing receptor agonists, or by any other means that induce rapid $Ca^{2+}$ changes.

In a preferred embodiment of the invention, the TRPM5 channel is activated by a calcium ionophore. A calcium ionophore is a small hydrophobic molecule that dissolves in lipid bilayer membranes and increases permeability to calcium. Examples of calcium ionophores include ionomycin, calcimycin A23187, and 4-bromocalcimycin A23187 (Sigma-Aldrich catalog 2004/2005, incorporated herein by reference).

In a preferred embodiment, the ion permeability of TRPM5 is measured in intact cells, preferably HEK-293 cells, which are transformed with a vector comprising nucleic acid encoding TRPM5 and an inducible promoter operably linked thereto. After inducement of the promotor, the TRPM5 polypeptides are produced and form a TRPM5 channel. Endogenous levels of intracellular ions are measured prior to inducement and then compared to the levels of intracellular ions measured subsequent to inducement. Fluorescent molecules such as SBFI and PBFI can be used to detect intracellular monovalent cation levels. TRPM5 permeability to $Na^+$, $K^+$, $Cs^+$ and to other monovalent cations can be measured in this assay.

The monovalent cationic permeability of the TRPM5 channel is increased when the channels are opened. The monovalent cationic permeability of the TRPM5 channel is decreased when the channels are closed.

The candidate bioactive agents can, for example, open TRPM5 channels in a variety of cells such as cells of the nervous, immune, and muscular systems of vertebrates. The opening of the TRPM5 channels may, for example, result in a decreased or reduced immune response in vertebrates. Bioactive agents such as the ones described herein are useful in the treatment of diseases, conditions associated with diseases, or disorders, such autoimmune or graft versus host diseases, or other related autoimmune disorders, wherein the decreased or reduced immune response results in an improved condition of the vertebrate (i.e., the disease, condition associated with the disease, or disorder is prevented, eliminated or diminished).

In still a further embodiment, the candidate bioactive agents can, for example, close TRPM5 channels in a variety of cells such as cells of the nervous, immune, and muscular systems of vertebrates. The closing of the TRPM5 channels may, for example, result in an enhanced or augmented immune response in vertebrates. Bioactive agents such as the ones described herein are useful in the treatment of diseases, conditions associated with diseases, or disorders such as breast and colon cancer, or other forms of cancer, wherein an enhanced or augmented immune response results in the improved condition of the vertebrate (i.e., the disease, condition associated with the disease, or disorder is prevented, eliminated or diminished).

The TRPM5 channel is also implicated in the release of insulin. Since the channel in its open state will cause the cell membrane potential to depolarize, the channel triggers electrical activity in cells that possess voltage-sensitive channels such as voltage-activated Na+ and Ca2+ channels. This is then followed by Ca2+ influx into such excitable cells and leads to exocytosis, which in some cells manifests itself in the release of neurotransmitters or hormones. Since electrical excitation is also a feature of insulin-secreting cells, and TRPM5 is expressed in pancreatic beta cells, TRPM5 is implicated in depolarizing beta cells, which ultimately causes insulin release.

Another embodiment provides for screening for candidate bioactive agents which modulate expression levels of TRPM5 within cells. Candidate agents can be used which wholly suppress the expression of TRPM5 within cells, thereby altering the cellular phenotype. In a further preferred embodiment, candidate agents can be used which enhance the expression of TRPM5 within cells, thereby altering the cellular phenotype. Examples of these candidate agents include antisense cDNAs and DNAs, regulatory binding proteins and/or nucleic acids, as well as any of the other candidate bioactive agents herein described which modulate transcription or translation of nucleic acids encoding TRPM5.

Yet another embodiment of the invention provides for methods of verifying that a candidate bioactive agent is capable of binding to TRPM5, modulating the monovalent cationic permeability of a TRPM5 channel, or modulating expression of a TRPM5 polypeptide. Methods of verification find use, for example, in clinical or diagnostic applications where a bioactive agent has been putatively identified as binding to TRPM5, modulating the monovalent cationic permeability of a TRPM5 channel, or modulating expression of a TRPM5 polypeptide. Methods of verification can be, for example, the assays described above for screening candidate bioactive agents for binding to TRPM5 or modulating TRPM5 monovalent cation permeability or modulating TRPM5 expression.

In still another embodiment, the invention provides antibodies which specifically bind to unique epitopes on the TRPM5 polypeptide, e.g., unique epitopes of the protein comprising amino acids from 1 through about 1165 of SEQ ID NO:2 (FIG. 7). Such antibodies can be assayed not only for binding to TRPM5 but also for their ability to modulate TRPM5 monovalent cation permeability.

The anti-TRPM5 polypeptide antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the TRPM5 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-TRPM5 polypeptide antibodies may further comprise monoclonal antibodies. Such monoclonal antibodies in addition to binding a TRPM5 polypeptide can also be identified as a bioactive candidate agent which modulates TRPM5 channel monovalent cation permeability. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the TRPM5 polypeptide or a fusion protein thereof. Generally, either peripheral blood lymphocytes ("PBLs") are used if cells of human origin are desired, or spleen cells, kidney cells, or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against a TRPM5 polypeptide. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The anti-TRPM5 polypeptide antibodies may further comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-TRPM5 polypeptide antibodies may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by the introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The anti-TRPM5 polypeptide antibodies may further comprise heteroconjugate antibodies. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a further embodiment, the anti-TRPM5 polypeptide antibodies may have various utilities. For example, anti-TRPM5 polypeptide antibodies may be used in diagnostic assays for TRPM5 polypeptides, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Further, TRPM5 antibodies may be used in the methods of the invention to screen for their ability to modulate the permeability of TRPM5 channels to monovalent cations.

EXAMPLES

Example 1

Generation of HEK-293 Cells Expressing TRPM5

Stable HEK-293 clones in which the CMV (cytomegalovirus) promoter induces high levels of TRPM5 transcripts were generated.

For RT-PCR, primer primers generally were designed in a way that the amplified product had to extend at least over one intronic region and amplified cDNA products were in the range of 150-500 bp. Northern blots were made as follows: total RNA was purified from cell cultures using RNeasy (Qiagen) according to the manufacturer's protocols. Concentration was determined photometrically. 20 µg of sample was electrophoresed on a 1.2% denaturing gel (Ix MOPS), transferred, and hybridized at 65° C. (high stringency) with a $^{32}P$-labeled probe (gelpurified and sequenced cDNA fragment) in the case of TRPM5 representing nucleotides 2529-3025 of the human full-length TRPM5 sequence (NCBI Accession number NM_014555) in ExpressHyb hybridization solution (Clontech), washed according to the manufacturer's high-stringency washing protocol, and autoradiographed (RPN-9, Amersham) for 1-3 days at –80° C. with intensifying screen (Amersham).

Human TRPM5 cDNA containing the complete ORF of the long splice version (Prawitt, D. et al., *Hum. Mol. Genet.* 9, 203-16 (2000)). was cloned into a XhoI/XbaI digested pcDNA3 (Invitrogen) vector using a pBKS+ intermediate and verified by sequencing. The ORF without the stop codon of the Enhanced-Green-Fluorescent-Protein (EGFP) was PCR amplified with primers containing flanking restrictions sites for Kpn1 (5'AAAAAGGTACCGCCACCATGGTGAGC-MGGGCGAGG, SEQ ID NO: 3; also creating a Kozak ideal initiation site for translation) and Xho1 (5'-AAAACTC-GAGCCCTTGTACA GCTCGTCCATGC, SEQ ID NO: 4) on pBI-EGFP vector DNA (Clontech), the PCR product was cloned directionally into the Kpn1/Xho1 restricted pcDNA3-TRPM5 constructs, fusing EGFP with the N-terminal part of TRPM5 after translation. Clones were verified by complete sequencing. The constructs were linearized by Pvu1 digestion and transfected into HEK-293 cells using electroporation (Biorad) at 960 µF, 0.3 KV in 0.4 cm electroporation vials. The transfected cells were selected by growth in DMEM medium containing 1.37 mg/ml G418 (PAA). Selective medium was changed every second day and selection was kept for at least 2 weeks. Single surviving cell clones were then isolated in a 24 well plate. Populations were frozen at early passage numbers, and these stocks were used for further studies. Stable clones that expressed the mRNAs were identified by Northern blot analysis (FIG. 1A). As negative control, stable clones of HEK-293 cells containing the empty expression construct backbone were generated.

As discussed above, the TRPM5 was EGFP-tagged in the N-terminal region. As shown in the confocal laser microscopic analyses of FIG. 1B, EGFP-TRPM5 expression is easily detectable by excitation with light of 489 nm wavelength and a significant fraction of the protein is localized to the plasma membrane.

HEK-293 (human embryonic kidney cells), WT128 and G401 (human Wilm's tumor cells), Hela, Jurkat (human T-cells), MIN (mouse 13-cells) and stably transfected HEK-293 cells expressing pcDNA3, pcDNA3-TRPM5 and pcDNA3-EGFP-TRPM5 were cultured at 37° C./5% CO2 in DMEM (PAN) containing 10% FCS (Min cells 15% FCS) and 2 mM glutamine. The media were supplemented with Penicillin (100 IU/ml)/Streptavidin (100 µg/ml; Invitrogen) and in the case of the transfected clones also supplemented with G418 (1.37 mg/ml; PAA). Ramos (human Burkitt lymphoma cells) and Cath.a (murine neuronal cells) cells were kept in RPMI 1640 (Sigma) medium supplemented with 1 mM Sodiumpyruvate, 0.15% (w/v) NaHCO$_3$, 10 mM Hepes, 2 mM L-glutamine, 0.25% glucose and in the case of Ramos cells with 10% FCS, in the case of Cath.a with 10% horse serum and 5% FCS. A20 (murine fibroblasts) were kept in IMDM medium (Gibco BRL), containing 0.05 µM β-mercapto-ethanol, 1 mM Sodiumpyruvate, 2 mM L-glutamine, 0.3% sodium Carbonate and 10% FCS. HEK-293 cells transfected with the TRPM5/pcDNA3 construct were grown on glass coverslips with DMEM medium supplemented with 10% FCS.

Cells grown on glass coverslips were transferred to the recording chamber and kept in a standard modified Ringer's solution of the following composition (in mM): NaCl 140, KCl 2.8, CaCl$_2$ 1, MgCl$_2$ 2, glucose 10, Hepes.NaOH 10, pH 7.2, with osmolarity typically ranging from 298-308 mOsm. Intracellular pipette-filling solutions contained (in MM): K-glutamate 120, NaCl 8, MgCl$_2$ 1, K-BAPTA 10, HEPES.CsOH, pH 7.2 adjusted with KOH. In order to adjust free [Ca$^{2+}$]i, to the desired concentration appropriate amounts of CaCl$_2$ were added as calculated with WebMaxC v2.1 (available through Stanford University). In the case of fura-2 measurements intracellular K-BAPTA was replaced by 200 µM fura-2. Fura-2 is a calcium indicator (*Handbook of Fluorescent Probes and Research Chemicals,* 9th ed. Molecular Probes). Solution changes were performed by pressure ejection from a wide-tipped pipette. Thrombin (NaCl-based buffer) was purchased from Sigma.

Example 2

Analysis of TRPM5: TRPM5 is a Calcium-Activated Channel

Cells expressing TRPM5 were prepared as in Example 1. The cells were perfused with an internal solution in which the free Ca$^{2+}$ concentration was buffered to 500 nM with an appropriate mixture of BAPTA and CaCl$_2$. Using this protocol, which does not induce store depletion, large membrane currents that activated immediately following establishment of the whole-cell configuration and quickly inactivated so as to produce a transient current response (FIG. 1C) were observed. The activation kinetics of TRPM5 currents under these experimental conditions is characterized by a half-time to peak of –3 s, with the peak current itself at –10 s. The current inactivates similarly rapidly to basal levels with a half-time of —13 s. Such currents were never observed in WT cells, suggesting that HEK-293 expressing TRPM5 are endowed with ion channels that respond to increases in [Ca$^{2+}$]i, thus indicating that TRPM5 is a Ca$^{2+}$-activated cation channel.

As illustrated in FIG. 1D, the current-voltage relationship of TRPM5 currents is distinctively outwardly rectifying with a reversal potential of –5±0.2 mV (n=51). This rectification is not due to single-channel amplitudes or permeation properties, but rather caused by a strong voltage-dependence, where positive membrane voltages favor channel opening and negative voltages reduce their open probabilities. This voltage dependence is characteristic of TRPM5 and significantly more pronounced than the voltage dependence of TRPM4.

The magnitude of TRPM5 currents is dependent on the level of [Ca$^{2+}$]i, which triggers increases in channel activity up to 1 µM, but then becomes inhibitory, resulting in a bell-shaped dose response curve (FIG. 1E). The dose-response curves fitted to these data yields EC50 values of 850 nM for activation and an IC$_{50}$ of 1.1 µM for inhibition, with a peak around 1 µM. Both curves are characterized by a rather high cooperativity (Hill coefficients of 4 and –6, respectively). At –80 mV, the average peak amplitudes of inward currents obtained with [Ca$^{2+}$]i of 1 µM was –440 pA±270 pA (n=5). This behavior sets TRPM5 further apart from TRPM4, whose activity plateaus at high levels of [Ca$^{2+}$]i, without signs of inhibition at levels up to 1.3 µM (Ref. 9 and data not shown).

Another striking feature is the pronounced and rapid inactivation of TRPM5 currents, which was observed at all Ca$^{2+}$ concentrations, suggesting that it is not directly mediated by Ca$^{2+}$, but rather represents an intrinsic property of TRPM5 or alternatively is caused by a regulatory mechanism. Since inactivation occurs while the activation is in progress, the theoretical peak amplitudes of TRPM5 currents are likely much higher than the 2 nA that are observed. The transient nature of these currents is a distinctive feature of TRPM5, setting it apart from the persistent activation of TRPM4. It should be noted that HEK-293 cells do express low levels of endogenous TRPM4 channels, but these do not contribute significantly to the currents shown in FIG. 1C, since they typically activate with a delay of 50 s and amount to only about 200 pA of outward current at +80 mV under these conditions9.

As shown in FIG. 1D, TRPM5 currents are characterized by strong outward rectification with a reversal potential around 0 mV, suggesting that it represents a non-selective ion permeation pathway. Thus, the outward current is carried by K+ ions and the inward current is be carried by the dominant extracellular ion species Na+ (i.e. [Na+]o/[K+]i). Several ion substitution experiments were performed where the main extracellular and intracellular ion species were [Na+]o/[Cs+]i or [K+]o/[K+]i or [K+]o/[Cs+]i and in all cases, the current-voltage relationships were very similar to the ones shown in FIG. 1D, suggesting that TRPM5 is similarly permeable for Na+, K+, and Cs+.

Experimental Methods

Calcium Measurements

The cytosolic calcium concentration was monitored at a rate of 5 Hz with a photomultiplier-based system using a monochromatic light source tuned to excite fura-2 fluorescence at 360 and 390 nm for 20 ms each (TILL Photonics, Munich, Germany). Emission was detected at 450-550 run with a photomultiplier, whose analog signals were sampled and processed by X-Chart software (HEKA, Lambrecht, Germany). Fluorescence ratios were translated into free intracellular calcium concentration based on calibration parameters derived from patch-clamp experiments with calibrated calcium concentrations.

Patch-Clamp Experiments

Patch-clamp experiments were performed in the tight-seal whole-cell configuration at 21-25° C. High-resolution current recordings were acquired by a computer-based patch-clamp amplifier system (EPC-9, HEKA, Lambrecht, Germany). Patch pipettes had resistances between 2-4 MS2 after filling with the standard intracellular solution. Immediately following establishment of the whole-cell configuration, voltage ramps of 50 ms duration spanning the voltage range of –100 to +100 mV were delivered from a holding potential of 0 mV at a rate of 0.5 Hz over a period of 300 to 600 seconds. All voltages were corrected for a liquid junction potential of 10 mV between external and internal solutions when using glutamate as intracellular anion. Currents were filtered at 2.9 kHz and digitized at 100 ps intervals. Capacitive currents and series resistance were determined and corrected before each voltage ramp using the automatic capacitance compensation of the EPC-9. The low-resolution temporal development of membrane currents was assessed by extracting the current amplitude at –80 and +80 mV from individual ramp current records. Where applicable, statistical errors of averaged data are given as means±S.E.M. with n determinations and statistical significance was assessed by Student's t-test. For single channel measurements inside-out patches were pulled into a modified standard external solution that contained no Ca$^{2+}$ and had 1 mM Na-EDTA. To record single channels a ramp protocol of 4.5 s from –100 mV to +100 mV and digitized at 280 ps was given with no wait time in between ramps. Ramps that had no channel activity during Ca$^{2+}$ application were used for leak correction and subtracted form all ramps acquired. Data collection was at 2.9 kHz filter setting and digitally filtered at 50 Hz for display purposes.

Example 3

Analysis of TRPM5: TRPM5 Does Not Carry $Ca^{2+}$

Figure 2:
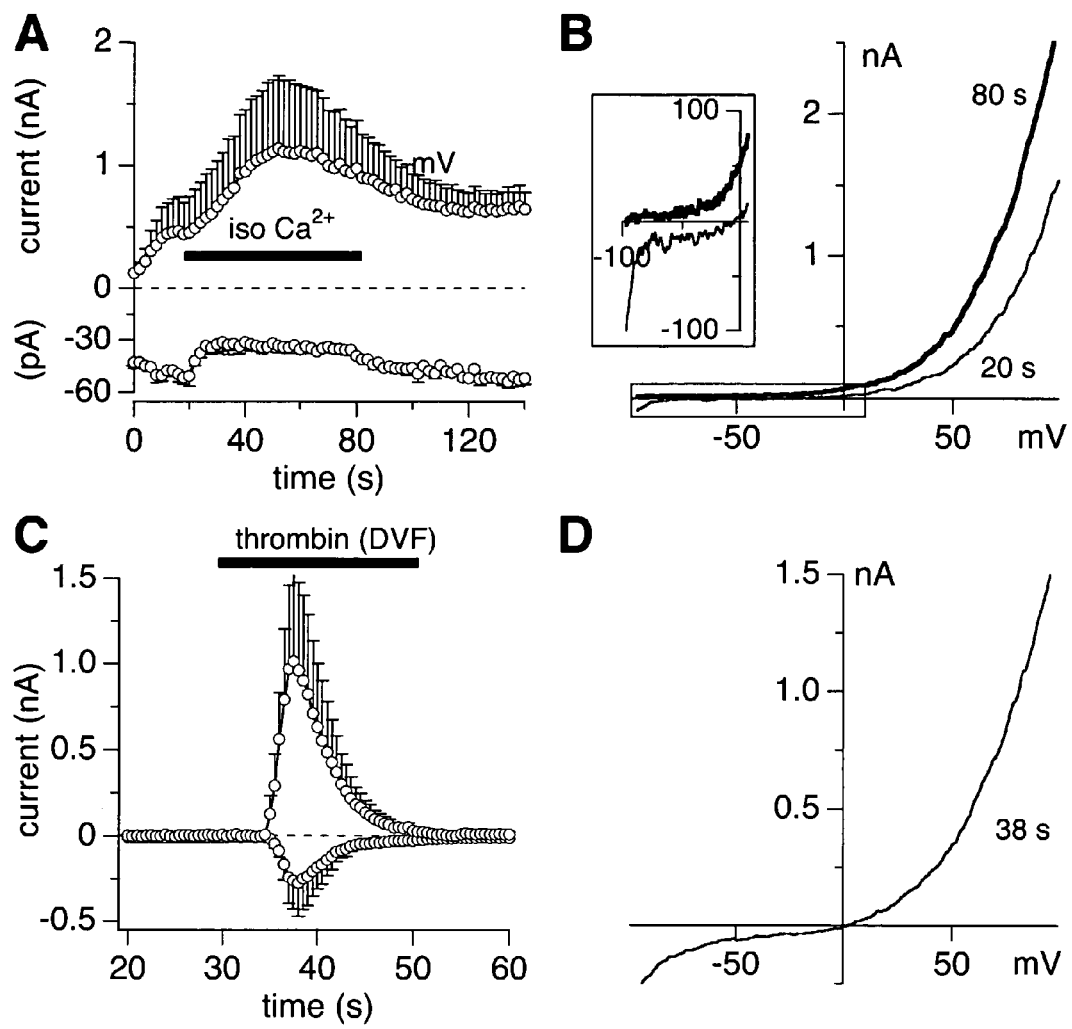
FIGS. 2A-D depict studies showing that TRPM5 is a monovalent cation channel.

TRPM5 was activated by 500 nM $[Ca^{2+}]i$ while cells were bathed in the standard extracellular solution and subsequently exposed to isotonic $CaCl_2$ solution (120 mM). As can be seen in FIG. 2A, this resulted in complete suppression of inward current and a slightly increased outward current. The current-voltage relationship under these conditions is illustrated in FIG. 2B, demonstrating that the inward current at negative potentials, initially carried by Na+, is completely suppressed when exposing cells to isotonic $Ca^{2+}$. In the absence of external Na+, the reversal potential shifts to negative potentials, due to the absence of a permeable ion that can carry inward current (inset of FIG. 2B). To further confirm that divalent ions do not permeate through TRPM5 channels, experiments were performed in which TRPM5 was activated by the $Ca^{2+}$-mobilizing receptor agonist thrombin (see also FIG. 3), which was applied in a divalent-free extracellular solution. Ion channels that carry divalent ions, e.g. TRPM7 (Nadler, M. J. et al., Nature 411, 590-5 (2001)) or the store-operated $Ca^{2+}$ current $I_{CRAC}$ (Hoth, M. & Penner, R., Nature 355, 353-6 (1992); Hoth, M. & Penner, R., J. Physiol. (Lond.) 465, 359-86 (1993)) normally produce large inward currents when cells are exposed to divalent-free solutions. As can be seen in FIG. 2C, inward currents remained significantly smaller than outward currents and the current-voltage relationship of TRPM5 currents under these conditions maintains strong outward rectification (FIG. 2E), suggesting that the smaller inward currents of TRPM5 under physiological conditions are not due to divalent ion permeation block. Thus, TRPM5 channels do not carry any appreciable amount of $Ca^{2+}$ and therefore are $Ca^{2+}$-activated nonselective (CAN) channels that are specific for monovalent cations.

Example 4

Analysis of TRPM5: TRPM5 is Activated by Elevations in Intracellular $Ca^{2+}$ Levels Under physiological conditions, TRPM5 currents would be expected to activate following receptor stimulation with agonists that couple to InsP3 production, as this leads to elevations in $[Ca^{2+}]i$. This theory was tested by performing voltage-clamp experiments in which the membrane currents and $[Ca^{2+}]i$ were measured simultaneously following thrombin-mediated $Ca^{2+}$ release. Whole-cell currents were continuously monitored by voltage ramps. However, here the $[Ca^{2+}]i$ was not buffered to fixed levels, but instead the $[Ca^{2+}]i$ was allowed to vary freely. The changes in $[Ca^{2+}]i$ were monitored by fura-2.

Figure 3:
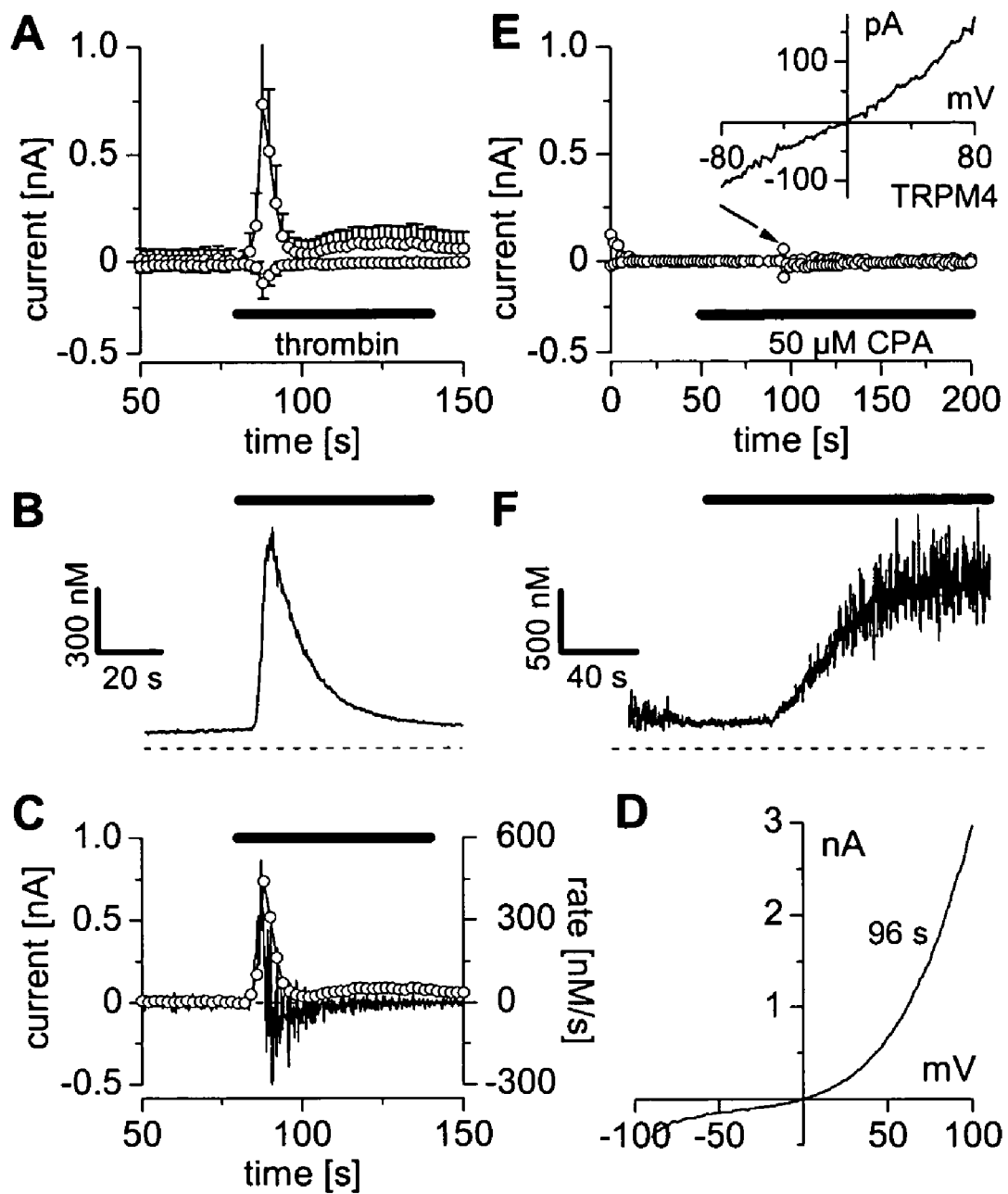
FIGS. 3A-F depict studies showing that TRPM5 activation is dependent on rate of calcium change. Data were obtained using combined patch-clamp and fura-2 recordings.

FIG. 3 illustrates the average response obtained under such experimental conditions (n=5). Thrombin stimulation, during the time indicated by the bar, resulted in a large $Ca^{2+}$-release transient (FIG. 3B) that was paralleled by a transient increase in inward and outward currents at +80 and −80 mV, respectively (FIG. 3A). The average current-voltage relationship obtained at the peak of the current, illustrated in FIG. 3F, shows strong outward rectification, which is characteristic of TRPM5. The strong activation of TRPM5 by $Ca^{2+}$ release sets it apart from TRPM4, which we is fairly unresponsive to short $Ca^{2+}$ release transients and requires $Ca^{2+}$ influx to fully activate (Launay, P. et al., Cell 109, 397-407 (2002)). The activation of TRPM5 by thrombin was entirely dependent on a rise in $[Ca^{2+}]i$, since inclusion of 10 mM BAPTA in the pipette solution consistently suppressed TRPM5 activation by thrombin (n=6, data not shown).

Close inspection of the kinetics of $[Ca^{2+}]i$ signals and current responses in FIG. 3 reveals that, although both occur concomitantly, the current response is very sharp, both in onset and decay and does not strictly mirror the levels in free $[Ca^{2+}]i$. Instead, the TRPM5 current response appears to reflect the rate of change in $[Ca^{2+}]i$, prompting the analysis of the $[Ca^{2+}]i$ signal in terms of rate of change in $[Ca^{2+}]i$ in comparison it to the actual current response. FIG. 3C illustrates this analysis by superimposing the time-derivative of the change in $[Ca^{2+}]i$ over time interval ($\Delta Ca^{2+}/\Delta t$, which reflects the rate of change in $[Ca^{2+}]i$ expressed in nM/s) on the appropriately scaled absolute current amplitude of TRPM5 at +80 mV. Indeed, the two traces are virtually identical, suggesting that the current closely follows the rate of change in $[Ca^{2+}]i$.

Experiments confirmed that the rate of change in $[Ca^{2+}]i$ rather than its absolute level is the primary determinant of TRPM5 activity. The experimental conditions were designed to elevate $[Ca^{2+}]i$ to levels similar to or even above those obtained by thrombin, but at a lower rate. Cyclopiazonic acid (CPA) which inhibits smooth endoplasmic reticulum $Ca^{2+}$ ATPases (Goeger, D. E., et. al., Biochem. Pharmacol. 37, 978-81 (1988)) and causes sustained elevations in $[Ca^{2+}]i$ that are characterized by a wave-like increase in $[Ca^{2+}]i$ with slow kinetics was used. FIGS. 3E and 3D illustrate a typical example of the changes in $[Ca^{2+}]i$ induced by CPA and the resulting currents at +80 and −80 mV, respectively. Although CPA increases $[Ca^{2+}]i$ well above 1 pM (panel E), it does so relatively slowly and fails to induce significant TRPM5 currents. Note that at the time indicated by the arrow in FIG. 4D, there is some activity of ion channels, but this is due to TRPM4, as evidenced by the current-voltage relationship and is entirely consistent with our previous reports. (Launay, P. et al. Cell 109, 397-407 (2002)). This indicates that TRPM5 currents indeed require fast changes in $[Ca^{2+}]i$ in order to build up significant current amplitude.

Example 5

Figure 4:
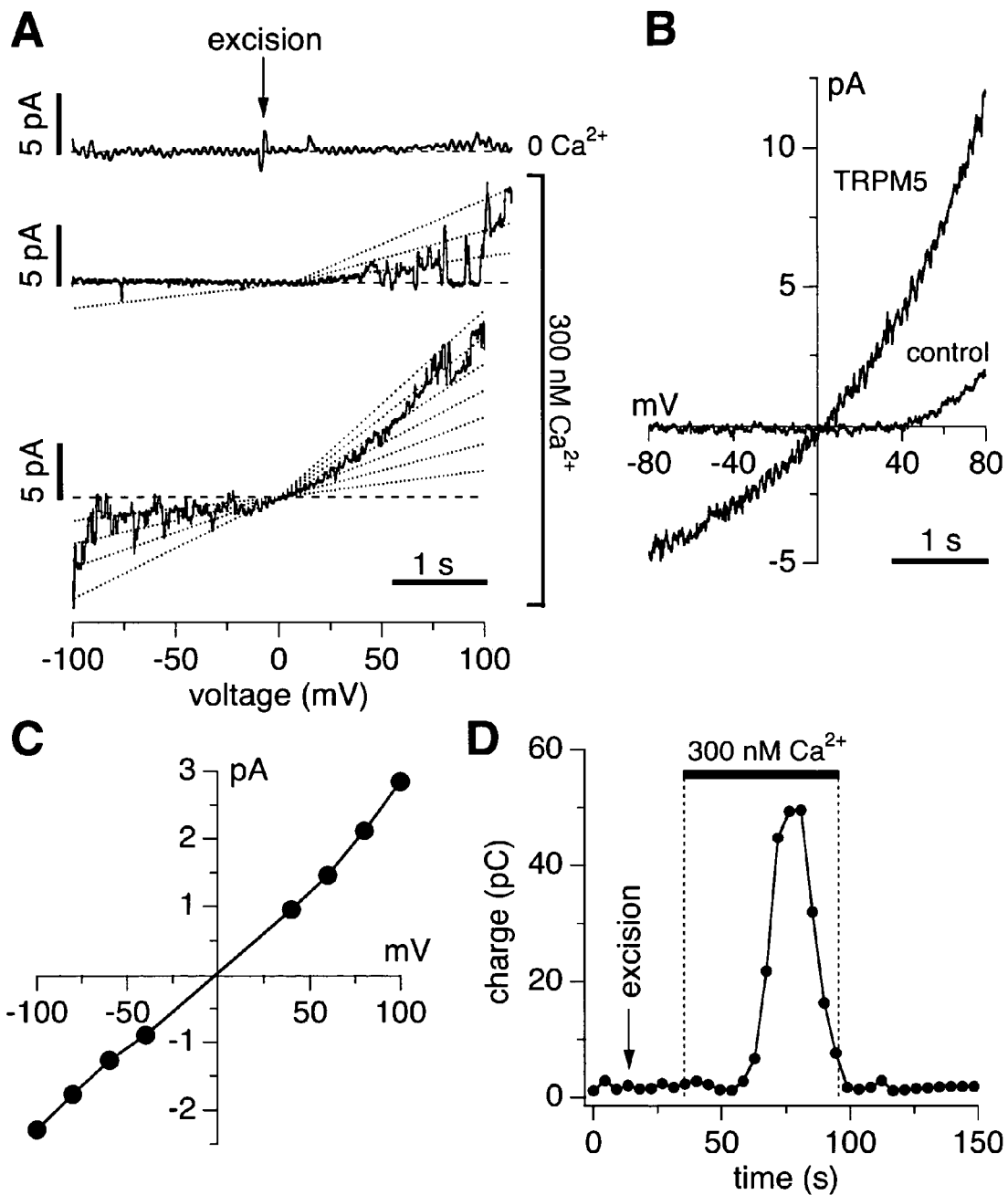
FIGS. 4 A-D depict studies showing that $Ca^{2+}$ activates TRPM5 single channels in inside-out patches.

Analysis of the Single Channel Properties of TRPM5 Using Membrane Patch Experiments The single-channel properties of TRPM5 were analyzed in cell-free excised membrane patches in the inside-out configuration of the patch-clamp technique. A similar voltage protocol as in whole-cell experiments was used, i.e. voltage ramps spanned the entire voltage range of −100 to +100 mV and were applied at regular intervals of 0.5 Hz from a holding potential of 0 mV. The only difference to the whole-cell protocol was that the ramp duration was extended to 4.5 s in order to maximize the chance of detecting channel openings at negative potentials, which are rare due to the extreme voltage-dependence of TRPM5 channels. FIG. 4A illustrates a representative experiment (n=5) in which a membrane patch containing at least 7 TRPM5 channels was initially excised in the inside-out configuration into a $Ca^{2+}$-free NaCl-based solution that additionally contained 1 mM EDTA (top panel; patch excision is marked by the arrow). The patch remained quiet until the cytosolic side of the patch was exposed to a potassium glutamate-based solution in which $Ca^{2+}$ was buffered to 300 nM (middle panels). A potassium glutamate-based solution was used to mimic the experimental conditions of the standard whole-cell experiments. Under these conditions, the activity of multiple channels was observed while the cytosolic side of the patch was exposed to elevated $Ca^{2+}$ and channel activity rapidly subsided as $Ca^{2+}$-free solution was reintroduced (bottom panel).

The TRPM5 channel activity showed strong voltage dependence in that positive potentials were characterized by both an increase in open probability as well as an increase in open times, which accounts for the strong outward rectification observed in both ensemble average of 75 single-channel current records (FIG. 4B) and the outward rectification observed in whole-cell recordings (FIG. 1D). The single-channel currents measured at discrete potentials show a linear current-voltage relationship (FIG. 4C), yielding a single-channel conductance of 25 pS as assessed by linear regression over the voltage range of −100 to +100 mV, which is identical to that of TRPM4 (Launay, P. et al., *Cell* 109, 397-407 (2002)).

Example 6

Analysis of TRPM5 in Pancreatic Beta Cells

Figure 5:
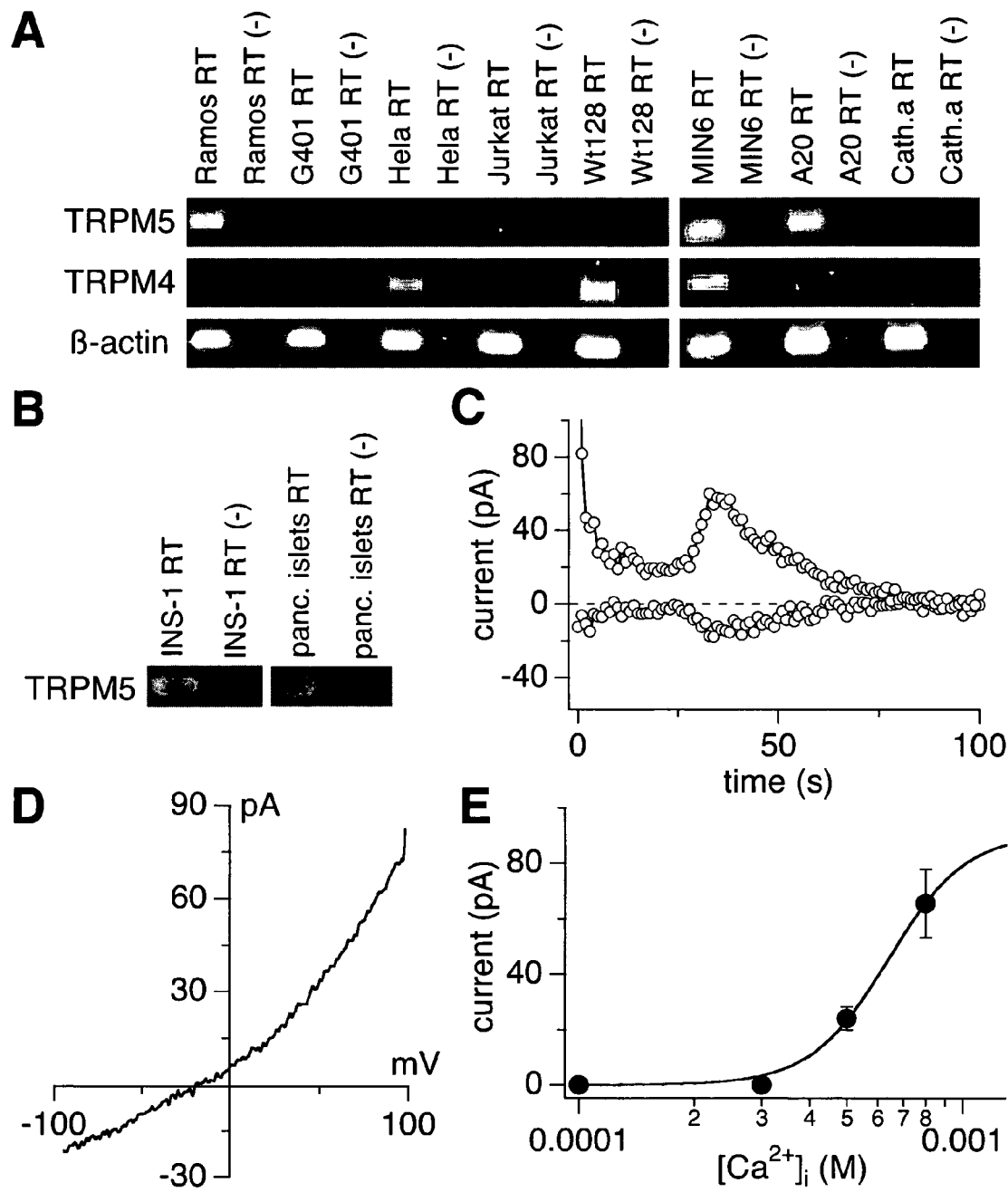
FIGS. 5A-E depict studies showing that rat insulinoma beta-cells INS-1 express endogenous TRPM5-1like currents.

TRPM5 is expressed in a variety of different tissues, including pancreatic beta cells (FIG. 5A). The presence of TRPM5 in pancreatic beta cells is of interest because diabetic Goto-Kakizaki (GK) rats, a genetic model for non-obese type-2 diabetes, have been reported to posses strongly reduced levels of TRPM5 (Irminger, J. et al. 38th *EASD Annual Meeting* Abstract #444 (2002)).

TRPM5 is found in another beta cell line, INS-1 (FIG. 5B). The INS-1 line was used to assess the electrophysiological features of TRPM5 in a native cellular context. Since the pancreatic beta-cell line INS-1 expressed TRPM5, the native TRPM5 currents in these cells was studied using the same experimental protocols that activated TRPM5 in the heterologous HEK-293 expression system (Examples 1-3). FIG. 5C illustrates that perfusing INS-1 cells with an intracellular solution that contained elevated levels of $Ca^{2+}$ (800 nM) induced a transient current, whose current-voltage relationship (FIG. 5D) was outwardly rectifying and closely resembled the current-voltage characteristics obtained for TRPM5 in the transfected HEK-293 cells. Similarly, the dose-response curve for activation of native TRPM5 currents in INS-1 cells is similar to that of TRPM5 in the heterologous system, although analysis could not be extended to $Ca^{2+}$ levels above 800 nM due to the massive activation of other $Ca^{2+}$-activated currents at higher $[Ca^{2+}]i$ The invention having been described, it will be apparent to ordinarily skilled artisans that numerous changes and modifications can be made thereto without departing from the spirit or the scope of the appended claims.

All publications and patents cited herein are expressly incorporated by reference for all purposes.

References

1. Clapham, D. E., Runnels, L. W. & Strubing, C. The TRP ion channel family. Nat. Rev. Neurosci. 2,387-96 (2001).
2. Minke, B. & Cook, B. TRP channel proteins and signal transduction. Physiol. Rev. 82, 42972(2002).
3. Montell, C., Birnbaumer, L. & Flockerzi, V. The TRP channels, a remarkably functional family. Cell 108, 595-8 (2002).
4. Harteneck, C., Plant, T. D. & Schultz, G. From worm to man: three subfamilies of TRP channels. Trends Neurosci. 23, 159-66 (2000).
5. Montell, C. et al. A unified nomenclature for the superfamily of TRP cation channels. Mol. Cell 9, 229-231 (2002).
6. Perez, C. A. et al. A transient receptor potential channel expressed in taste receptor cells. Nat. Neurosci. 5, 1169-76 (2002).
7. Zhang, Y. et al. Coding of sweet, bitter, and umami tastes: different receptor cells sharing similar signaling pathways. Cell 112, 293-301 (2003).
8. Prawitt, D. et al. Identification and characterization of MTR1, a novel gene with homology to melastatin (MLSN1) and the trp gene family located in the BWS-WT2 critical region on chromosome I 1p15.5 and showing allele-specific expression. Hum. Mol. Genet. 9, 203-16 (2000).
9. Launay, P. et al. TRPM4 is a Ca t+-activated nonselective cation channel mediating cell membrane depolarization. Cell 109, 397-407 (2002).
10. Gilbertson, T. A., Damak, S. & Margolskee, R. F. The molecular physiology of taste transduction. Curr. Opin. Neurobiol. 10, 519-27 (2000).
11. Margolskee, R. F. Molecular mechanisms of bitter and sweet taste transduction. J. Biol. Chem. 277,14 (2002).
12. Hoth, M. & Penner, R. Depletion of intracellular calcium stores activates a calcium current in mast cells. Nature 355, 353-6 (1992).
13. Parekh, A. B. & Penner, R. Store depletion and calcium influx. Physiol. Rev. 77, 901-30 (1997).
14. Parekh, A. B., Fleig, A. & Penner, R. The store-operated calcium current IcRAc: nonlinear activation by InsP3 and dissociation from calcium release. Cell 89, 973-80 (1997).
15. Nadler, M. J. et al. LTRPC7 is a Mg-ATP-regulated divalent cation channel required for cell viability. Nature 411, 590-5 (2001).
16. Hoth, M. & Penner, R. Calcium release-activated calcium current in rat mast cells. J. Physiol. (Lond.) 465, 359-86 (1993).
17. Goeger, D. E., Riley, R. T., Dorner, J. W. & Cole, R. J. Cyclopiazonic acid inhibition of the Ca t+-transport ATPase in rat skeletal muscle sarcoplasmic reticulum vesicles. Biochem. Pharmacol. 37, 978-81 (1988).
18. Enklaar, T. et al. Mtr1, a novel biallelically expressed gene in the center of the mouse distal chromosome 7 imprinting cluster, is a member of the Trp gene family. Genomics 67, 179-87 (2000).
19. Irminger, J. et al. Identification of differentially expressed genes in islets of diabetic GK rats, using subtractive hybridization. 38'h EASD Annual Meeting Abstract #444 (2002).
20. Gilon, P. & Henquin, J. C. Mechanisms and physiological significance of the cholinergic control of pancreatic beta-cell function. Endocr. Rev. 22, 565-604 (2001).
21. Gilon, P., Ravier, M. A., Jonas, J. C. & Henquin, J. C. Control mechanisms of the oscillations of insulin secretion in vitro and in vivo. Diabetes 51 Suppl 1, S 144-51 (2002).

What is claimed is:

1. A method for screening for a candidate agent capable of modulating monovalent cation permeability of a Transient Receptor Potential Melastatin-like 5 (TRPM5) channel, wherein said TRPM5 channel comprises a polypeptide having the amino acid sequence according to SEQ ID NO: 2, the method comprising:
   a) providing a recombinant cell comprising a recombinant nucleic acid encoding said polypeptide and an inducible promoter operably linked thereto;
   b) inducing the recombinant cell to express the TRPM5 polypeptide and form a TRPM5 channel comprising the TRPM5 polypeptide;
   c) contacting the recombinant cell with a candidate agent;
   d) activating the TRPM5 channel; and
   e) detecting modulation of monovalent cation permeability of the TRPM5 channel.

2. The method of claim 1, wherein the monovalent cation is selected from the group consisting of $Na^{30}$, $K^{30}$, and $Cs^{30}$.

3. The method of claim 1, wherein the monovalent cation permeability of the TRPM5 channel is increased by the contacting with the candidate agent.

4. The method of claim 1, wherein the monovalent cation permeability of the TRPM 5-channel is decreased by the contacting with the candidate agent.

5. The method of claim 1, wherein the method further comprises contacting the cell with a monovalent cation indicator.

6. The method of claim 5, wherein the indicator comprises a fluorescent molecule.

7. The method of claim 6, wherein the fluorescent molecule comprises sodium-binding benzofuran isophthalate (SBFI).

8. The method of claim 5, wherein the modulation is detected with the indicator.

9. The method of claim 1, wherein the contacting with the candidate agent alters the membrane potential of the recombinant cell.

10. The method of claim 9, wherein the membrane potential of the recombinant cell is monitored with a membrane potential sensitive probe.

11. The method of claim 10, wherein the membrane potential sensitive probe is bis-(1,3-dibutylbarbituric acid)trimethine oxonol (DiBAC4(3)).

12. The method of claim 1, wherein the TRPM5 channel is activated by a calcium ionophore.

13. A method for measuring monovalent cation permeability of a Transient Receptor Potential Melastatin-like 5 (TRPM5) channel, wherein said TRPM5 channel comprises a polypeptide having the amino acid sequence according to SEQ ID NO: 2, the method comprising:
   a) providing a recombinant cell comprising a recombinant nucleic acid encoding aTRPM5 polypeptide;
   b) expressing the TRPM5 polypeptide and forming a channel comprising the TRPM5 polypeptide;
   c) activating the TRPM5 channel; and
   d) detecting the monovalent cation permeability of the TRPM5 channel.

14. The method of claim 13, wherein the monovalent cation is selected from the group consisting of $Na^{30}$, $K^{30}$, and $Cs^{30}$.

15. The method of claim 13, wherein the method further comprises contacting the cell with a monovalent cation indicator.

16. The method of claim 15, wherein the indicator comprises a fluorescent molecule.

17. The method of claim 16, wherein the fluorescent molecule comprises sodium-binding benzofuran isophthalate (SBFI).

18. The method of claim 15, wherein the monovalent cation is detected with the indicator.

19. The method of claim 13, further comprising contacting the recombinant cell with a candidate agent.

20. The method of claim 13, wherein the measuring further comprises comparing the intracellular monovalent cation levels in said recombinant cell to intracellular monovalent cation levels in a cell which does not express the TRPM5 polypeptide.

21. The method of claim 19, wherein the measuring further comprises comparing the intracellular monovalent cation levels in said recombinant cell to intracellular monovalent cation levels in a cell which does not express the TRPM5 polypeptide but which is in contact with the candidate agent.

22. The method of claim 13, wherein the TRPM5 channel is activated by a calcium ionophore.

23. A method for screening for a candidate agent capable of modulating monovalent cation permeability of a Transient Receptor Potential Melastatin-like 5 (TRPM5) channel, wherein said TRPM5 channel comprises a polypeptide having the amino acid sequence according to SEQ ID NO:2, the method comprising:
   a) providing a cell comprising a TRPM5 channel;
   b) contacting the cell with a candidate agent;
   c) activating said TRPM5 channel by increasing intracellular calcium concentration;
   d) detecting modulation of monovalent cation permeability of said TRPM5 channel by monitoring the membrane potential of the cell, wherein said monitoring comprises the use of a membrane potential-sensitive probe.

24. The method of claim 23, wherein said cell is a recombinant cell comprising a recombinant nucleic acid encoding the TRPM5 polypeptide and an inducible promoter operably linked thereto, and wherein said method further comprises the step of inducing said recombinant cell to express the TRPM5 polypeptide and form a TRPM5 channel comprising the TRPM5 polypeptide.

25. The method according to claim 23, further comprising:
   e) measuring intracellular calcium levels using an indicator specific for calcium;
   wherein a change in monovalent cation permeability concomitant with a change in intracellular calcium levels in the presence of said candidate agent indicates that said candidate agent is a TRPM5 channel-specific modulator.

26. The method of claim 25, wherein said cell is a recombinant cell comprising a recombinant nucleic acid encoding the TRPM5 polypeptide and an inducible promoter operably linked thereto, and wherein said method further comprises the step of inducing said recombinant cell to express the TRPM5 polypeptide and form a TRPM5 channel comprising the TRPM5 polypeptide.

* * * * *